(12) United States Patent
Judson et al.

(10) Patent No.: US 12,083,324 B2
(45) Date of Patent: Sep. 10, 2024

(54) DRIVE RIBBON FOR MOVING PISTON WITHIN CONTAINER

(71) Applicant: Eli Lilly and Company, Indianapolis, IN (US)

(72) Inventors: Jared Alden Judson, Medford, MA (US); Timothy L. Moulton, Newport, RI (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 0 days.

(21) Appl. No.: 18/306,760

(22) Filed: Apr. 25, 2023

(65) Prior Publication Data
US 2023/0256173 A1 Aug. 17, 2023

Related U.S. Application Data

(63) Continuation of application No. 17/125,493, filed on Dec. 17, 2020, now Pat. No. 11,642,467, which is a
(Continued)

(51) Int. Cl.
*A61M 5/315* (2006.01)
*A61M 5/24* (2006.01)

(52) U.S. Cl.
CPC ........ *A61M 5/31515* (2013.01); *A61M 5/315* (2013.01); *A61M 5/24* (2013.01);
(Continued)

(58) Field of Classification Search
CPC .... A61M 5/31515; A61M 5/315; A61M 5/24; A61M 5/31511; A61M 5/31501;
(Continued)

(56) References Cited

U.S. PATENT DOCUMENTS

| 4,313,439 A | 2/1982 | Babb et al. |
| 4,875,660 A | 10/1989 | Gagnon et al. |

(Continued)

FOREIGN PATENT DOCUMENTS

| CN | 1921899 A | 2/2007 |
| EP | 2238997 | 10/2010 |

(Continued)

OTHER PUBLICATIONS

Paco Spiralift (2017) Website. http://www.pacospiralift.com/.
(Continued)

*Primary Examiner* — Tasnim Mehjabin Ahmed
(74) *Attorney, Agent, or Firm* — M. Daniel Spillman

(57) ABSTRACT

A medical delivery device for advancing a piston in a medicament container to expel a medicament. A support structure supports the container and a drive assembly that advances the piston. The drive assembly includes a drive ribbon that can be retracted and extended. The retracted ribbon defines a spiral and the extended ribbon defines a helix. The drive ribbon is incrementally moveable between the retracted spiral configuration and extended helical configuration. A mechanical drive rotates the drive ribbon to selectively extend and retract the ribbon. A thrust member having a helical ramp engages a proximal edge of the drive ribbon where it transitions between a spiral and helix. A bearing member at the distal end of the drive ribbon exerts an axial force on the piston when the ribbon is extended.

20 Claims, 23 Drawing Sheets

Related U.S. Application Data continuation of application No. 16/080,130, filed as application No. PCT/US2017/022259 on Mar. 14, 2017, now Pat. No. 10,898,652.

(60) Provisional application No. 62/310,961, filed on Mar. 21, 2016.

(52) U.S. Cl.
CPC ............. *A61M 2005/31518* (2013.01); *A61M 2005/3152* (2013.01)

(58) Field of Classification Search
CPC .......... A61M 5/31576; A61M 5/31583; A61M 2005/31518; A61M 2005/3152; A61M 2005/31588
See application file for complete search history.

(56) References Cited

U.S. PATENT DOCUMENTS

| | | | |
|---|---|---|---|
| 5,178,609 A * | 1/1993 | Ishikawa | A61M 5/1454 604/131 |
| 5,478,316 A | 12/1995 | Bitdinger et al. | |
| 5,637,095 A | 6/1997 | Nason et al. | |
| 6,537,251 B2 | 3/2003 | Klitmose | |
| 6,547,216 B1 | 4/2003 | Bouchard et al. | |
| 7,066,909 B1 | 6/2006 | Peter et al. | |
| 7,213,796 B2 | 5/2007 | Laforest | |
| 7,220,248 B2 | 5/2007 | Mernøe | |
| 7,500,959 B2 | 3/2009 | Munk | |
| 8,517,991 B2 | 8/2013 | Clemente | |
| 10,898,652 B2 * | 1/2021 | Judson | A61M 5/31515 |
| 11,642,467 B2 * | 5/2023 | Judson | A61M 5/315 604/218 |
| 2001/0023637 A1 | 9/2001 | Klitmose et al. | |
| 2002/0091358 A1 | 7/2002 | Klitmose | |
| 2004/0045555 A1 | 3/2004 | Nelson et al. | |
| 2006/0276753 A1 | 12/2006 | Kronestedt et al. | |
| 2010/0094253 A1 | 4/2010 | Boyd et al. | |
| 2010/0249706 A1 | 9/2010 | Clemente | |
| 2011/0226264 A1 | 9/2011 | Friedman et al. | |
| 2011/0306929 A1 | 12/2011 | Levesque et al. | |
| 2012/0041387 A1 | 2/2012 | Brüggemann et al. | |
| 2012/0172817 A1 | 7/2012 | Brüggemann et al. | |
| 2014/0214001 A1 | 7/2014 | Mortazavi | |
| 2015/0290392 A1 | 10/2015 | Henderson et al. | |
| 2016/0158453 A1 | 6/2016 | Oakley | |
| 2017/0296750 A1 | 10/2017 | Morris | |

FOREIGN PATENT DOCUMENTS

| | | |
|---|---|---|
| EP | 2698180 | 2/2014 |
| JP | 2015524722 A | 8/2015 |
| JP | 2015221386 A | 12/2015 |
| KR | 20090082490 | 7/2009 |
| KR | 20170065622 | 6/2017 |
| WO | 2006066963 | 6/2006 |
| WO | 2010037759 | 4/2010 |
| WO | 2014138506 A1 | 9/2014 |
| WO | 2017099894 | 6/2017 |
| WO | 2017139741 | 8/2017 |

OTHER PUBLICATIONS

Patent Cooperation Treaty International Search Report and Written Opinion pertaining to International Application No. PCT/US2017/022259; Date of Mailing: May 31, 2017.

* cited by examiner

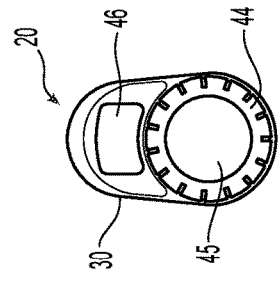
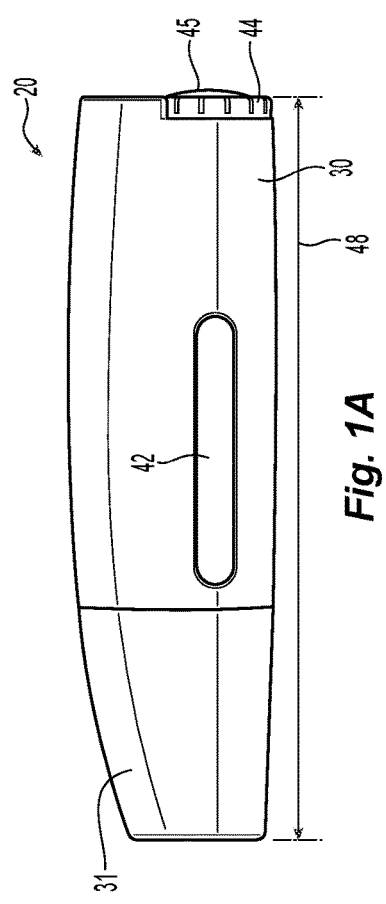
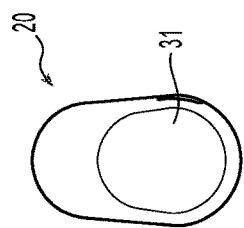
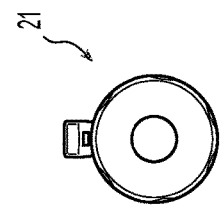
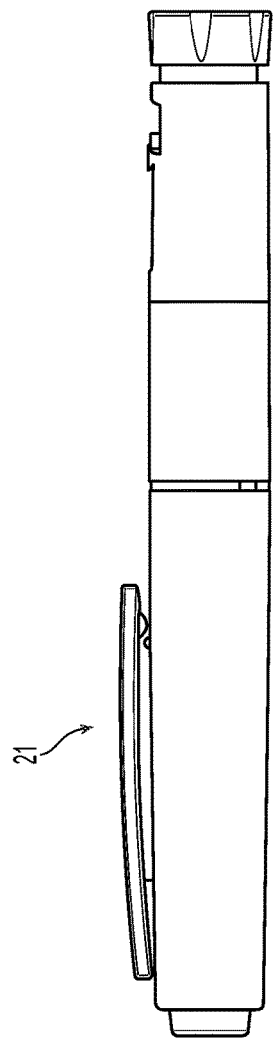
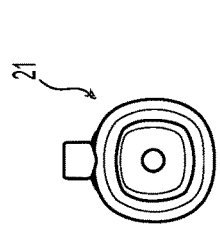
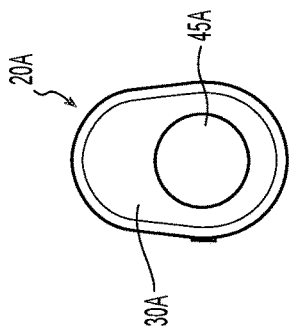
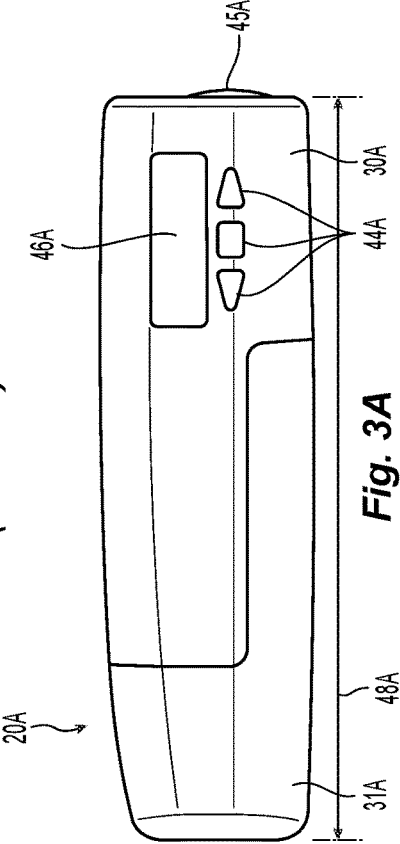
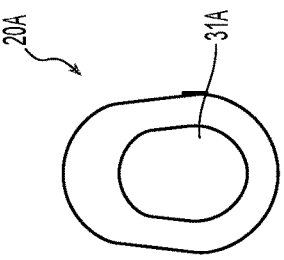

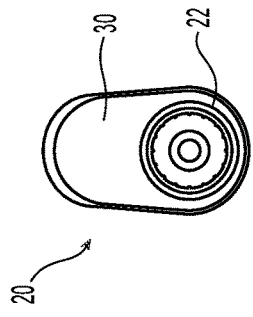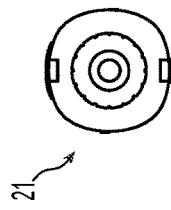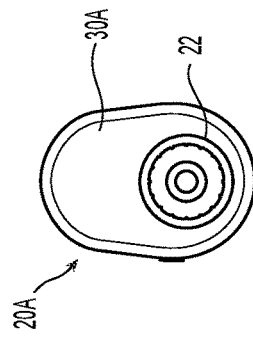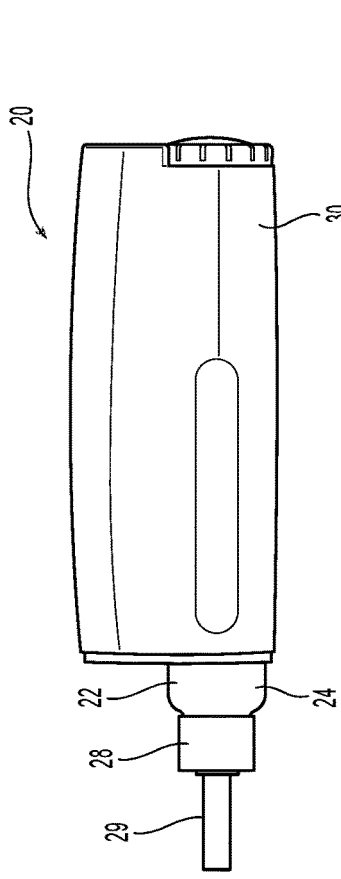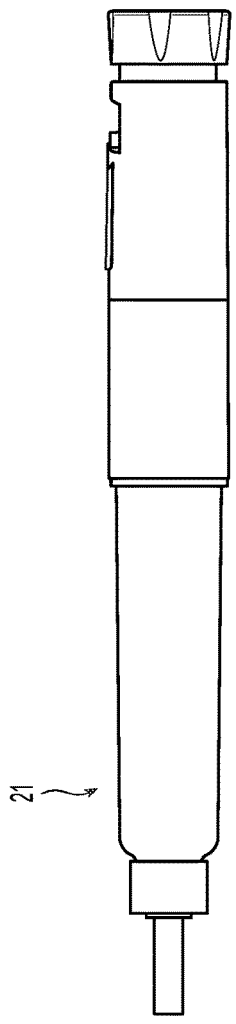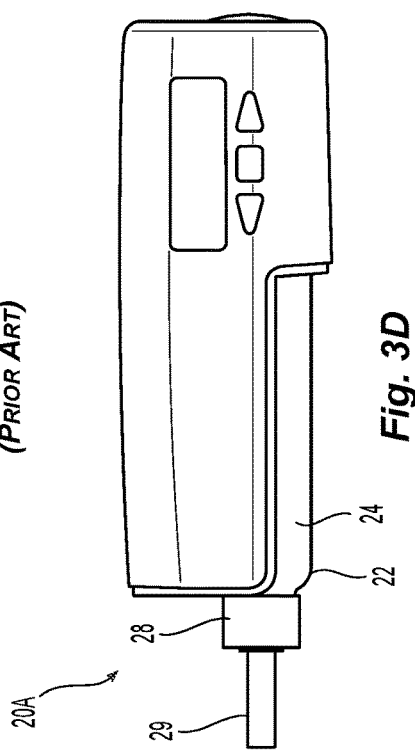
Fig. 1E
Fig. 2E (Prior Art)
Fig. 3E
Fig. 1D
Fig. 2D (Prior Art)
Fig. 3D

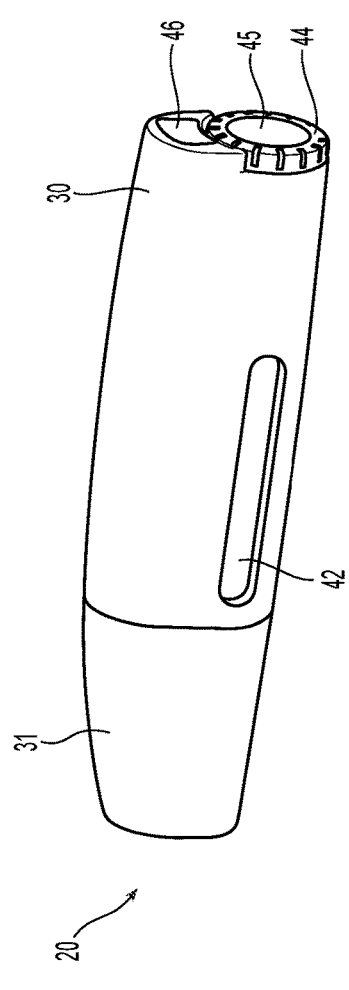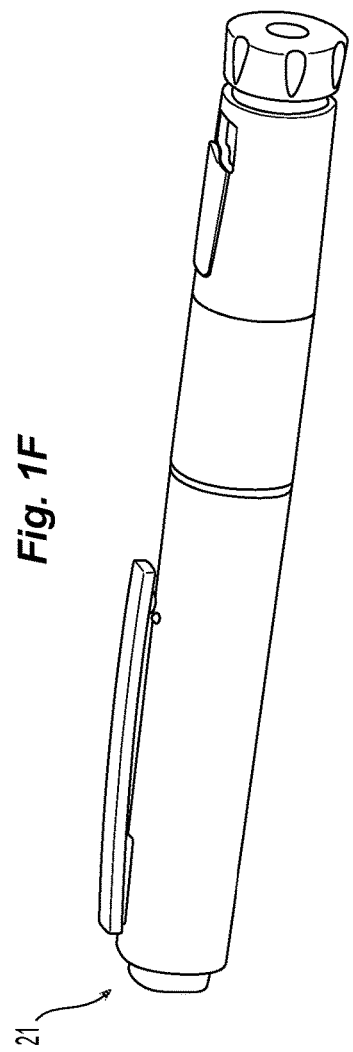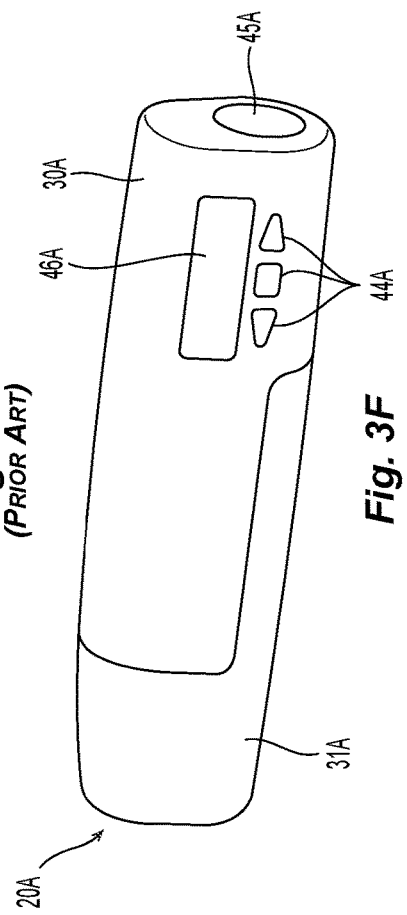

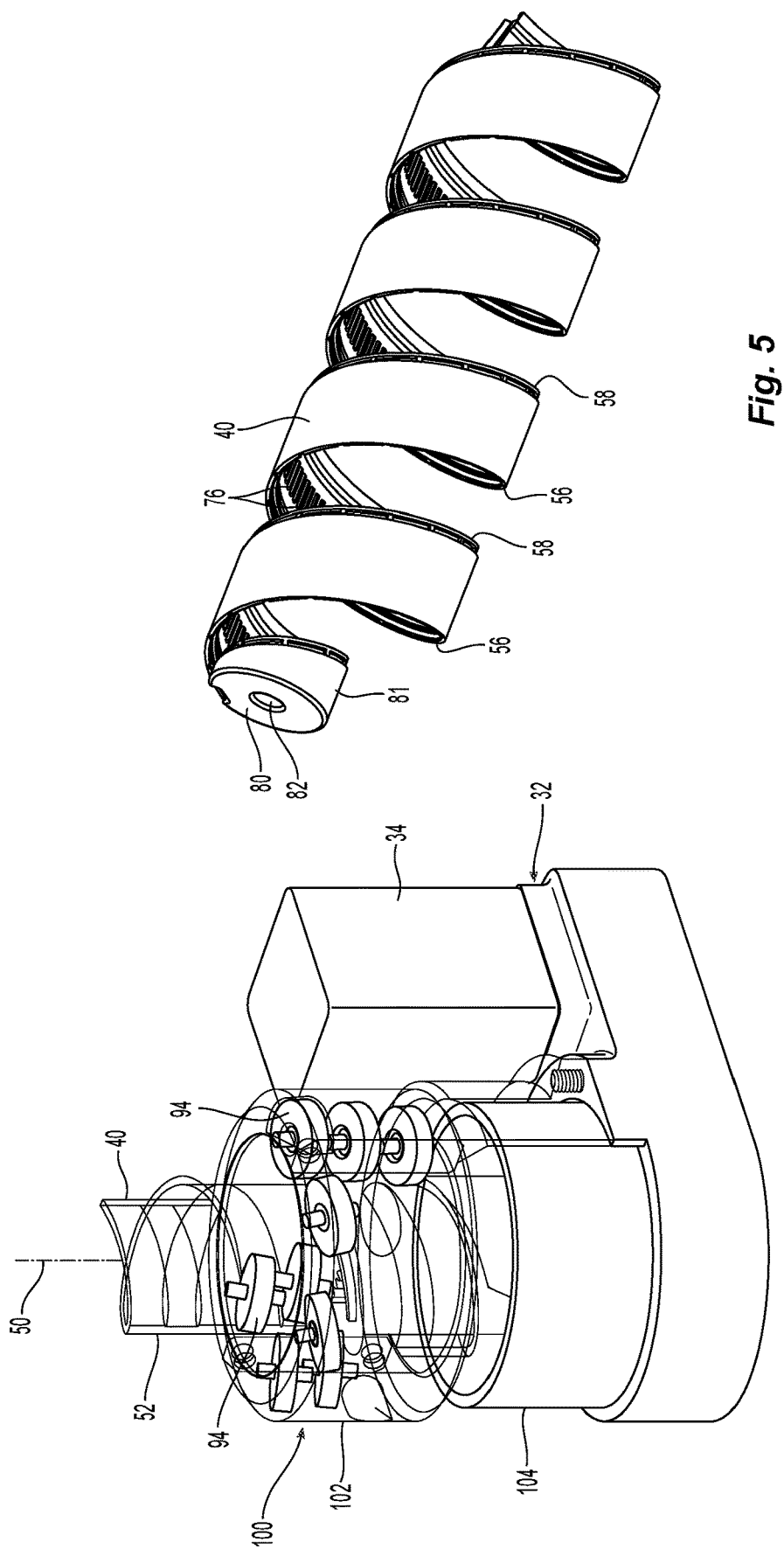

DRIVE RIBBON FOR MOVING PISTON WITHIN CONTAINER

This application is a continuation of U.S. patent application Ser. No. 17/125,493, filed Dec. 17, 2020, which is a continuation of U.S. patent application Ser. No. 16/080,130, filed Aug. 27, 2018, which is the National Stage of International Application No. PCT/US2017/022259, filed Mar. 14, 2017, which claims priority and the benefit of U.S. provisional patent application Ser. No. 62/310,961 filed on Mar. 21, 2016 entitled MEDICAL DELIVERY DEVICE WITH AXIALLY EXPANDABLE DRIVE MEMBER, the disclosure of which is hereby incorporated herein by reference.

BACKGROUND

The present invention relates to medical delivery devices such as injection devices.

Conventional injection devices are often used to inject a medicament into a patient.

For example, injection pens that receive disposable cartridges containing insulin are often used by diabetes patients. Such pens generally include an elongate rod that acts on a piston within the cartridge. As the rod advances the piston, the medicament within the cartridge is dispensed through a needle and into the patient.

The rod must project outwardly from the cartridge to engage a driving mechanism within the pen throughout the injection process including when the rod has reached the limit of forward advancement into the cartridge. The rod must also be accommodated within the pen when it is has been fully retracted so that the rod may be inserted into a fresh cartridge that is filled with medicament. As a result, conventional injection pens are generally elongate and thin with the length of the injection pen being more than twice the length of the cartridge barrel in which the medicament is contained. Similarly, for non-pen-shaped refillable injection devices, the length of the device is generally more than twice the length of the cartridge barrel in which the medicament is contained.

When such injection devices are used to self-administer the medicament at different times throughout the day, it is desirable for the injection device to be readily carried by the user. For example, diabetes patients often self-administer insulin using injection devices and carry the devices with them throughout the day. While conventional injection pens and similar devices are sufficiently small to be portable, the length of such devices often makes transport of the devices awkward.

SUMMARY

The present invention provides a compact and easily transported medical delivery device.

The invention comprises, in one form thereof, a medical delivery device for use with a medicament container. The medicament container has a container body holding the medicament, defines an outlet, and further includes a piston disposed within the container body wherein advancement of the piston in the container body expels medicament through the outlet. The delivery device includes a support structure adapted to support the medicament container and a drive assembly supported on the support structure and adapted to advance the piston within the container body. The drive assembly includes a drive ribbon having a distal edge section and a proximal edge section. The drive ribbon has a retracted configuration and an extended configuration wherein a retracted portion of the drive ribbon in the retracted configuration defines a spiral and an extended portion of the drive ribbon in the extended configuration defines a helix. The drive ribbon is incrementally moveable between the retracted and extended configurations and movement of the drive ribbon from the retracted configuration to the extended configuration defines a drive axis. A mechanical drive is operably coupled with the drive ribbon and selectively rotates the drive ribbon about the drive axis wherein rotation of the drive ribbon in a first direction extends the drive ribbon and rotation of the drive ribbon in an opposite second direction retracts the drive ribbon. A thrust member is operably disposed between the support structure and the drive ribbon and is engaged with at least a portion of the proximal edge section when the drive ribbon is at least partially extended. A bearing member is supported on the drive ribbon proximate a distal end of the drive ribbon. The bearing member is adapted to exert an axial force on the piston when the drive ribbon is being extended. The axial force exerted by the bearing member on the piston is at least partially transmitted to the support structure through the medicament container. When an axial compressive load is exerted on the drive ribbon, the axial compressive load is at least partially transmitted to the support structure through the thrust member.

In some embodiments, the support structure defines a housing adapted to be held in a human hand. In such embodiments, the medicament container may have a storage volume of at least 3 mL with the support structure defining an axial length of no more than 110 mm. The support structure may even define an axial length of no more than 100 mm.

In some embodiments of the delivery device, the thrust member is rotationally fixed relative to the support structure and defines a helical ramp engageable with the proximal edge section of the drive ribbon wherein, when the drive ribbon is rotated in the first direction, a transition portion of the drive ribbon engaging the helical ramp transitions from the retracted configuration to the extended configuration and, when the drive ribbon is rotated in the second direction, the transition portion of the drive ribbon engaging the helical ramp transitions from the extended configuration to the retracted configuration. In such embodiments, the delivery device may further include a ribbon bearing member circumscribing the thrust member exerting a radially inward bearing force on the drive ribbon proximate the helical ramp. The ribbon bearing member may take the form of a plurality of rollers engageable with the drive ribbon wherein the plurality of rollers exert the radially inward force and bias the drive ribbon onto the helical ramp of the thrust member as the drive ribbon is rotated. In those embodiments including a helical ramp, the retracted portion of the drive ribbon proximate the helical ramp defines a radius larger than the radius of the helical ramp.

In some embodiments of the delivery device, the bearing member includes a rotational bearing allowing relative rotational movement between the drive ribbon and the piston about the drive axis. Such a rotational bearing may take the form of a jewel bearing.

The delivery device may include, in some embodiments, a drive ribbon that defines a plurality of gear teeth engageable with the mechanical drive whereby the mechanical drive can rotate the drive ribbon by transmitting a rotational force through the plurality of gear teeth.

In some embodiments of the drive ribbon, the extended portion of the drive ribbon may have a proximal edge section that is directly bearingly engaged with an adjacent portion of the distal edge section. In such embodiments, one of the proximal and distal edge sections may define a radially extending lip to directly bearingly engage the other one of the proximal and distal edge sections. It is also possible in such embodiments for the one of the proximal and distal edge sections to define a plurality of projections and the other one of the proximal and distal edge sections to define a plurality of cooperating recesses.

The delivery device may have a drive ribbon which is a unitary one-piece ribbon wherein all of the axial forces transferred between the bearing member and the thrust member when the drive ribbon is at least partially extended are transferred by the unitary one-piece ribbon.

In some embodiments, the delivery device also includes a cylindrical bobbin wherein the retracted portion of the drive ribbon is stored in the bobbin. In such embodiments, the bobbin may be rotatably disposed on the thrust member. In embodiments including a bobbin, for the retracted portion of the drive ribbon disposed within the bobbin, the drive ribbon may be configured such that a distal edge surface of the drive ribbon lies in a first plane oriented perpendicular to the drive axis and a proximal edge surface of the drive ribbon lies in a second plane oriented perpendicular to the drive axis.

In some embodiments of the delivery device, the mechanical drive includes a battery powered motor.

In some embodiments of the delivery device, the proximal edge section defines a proximal edge surface and the distal edge section defines a distal edge surface with the proximal edge surface defining a first axially facing lengthwise portion and a second axial facing lengthwise portion and the distal edge surface defining a third axially facing lengthwise portion and a fourth axially facing lengthwise portion. In the extended portion of the drive ribbon defining a helix, the proximal edge section of the ribbon is engaged with an adjacent portion of the distal edge section with the second lengthwise portion of the proximal edge surface engaged with the third lengthwise portion of the distal edge surface and wherein the first lengthwise portion of the proximal edge surface and the fourth lengthwise portion of the distal edge surface extend radially outwardly in opposite directions. And, in such embodiments, the thrust member is engaged with the first lengthwise portion of the proximal edge surface. The thrust member may engage the first lengthwise portion of the proximal edge surface in a transition portion of the drive ribbon disposed between the retracted portion and extended portion of the drive ribbon.

The invention comprises, in another form thereof, a medical delivery device for use with a medicament container having a container body holding the medicament and defining an outlet. The medicament container further includes a piston disposed within the container body wherein advancement of the piston in the container body expels medicament through the outlet. The delivery device includes a support structure adapted to support the medicament container; and a drive assembly supported on the support structure and adapted to advance the piston within the container body. The drive assembly includes a drive ribbon having a distal edge section defining a distal edge surface and a proximal edge section defining a proximal edge surface. The drive ribbon has a retracted configuration and an extended configuration wherein a retracted portion of the drive ribbon in the retracted configuration defines a spiral and an extended portion of the drive ribbon in the extended configuration defines a helix. The drive ribbon is incrementally moveable between the retracted and extended configurations with movement of the drive ribbon from the retracted configuration to the extended configuration defining a drive axis. The proximal edge surface defines a first axially facing lengthwise portion and a second axially facing lengthwise portion and the distal edge surface defines a third axially facing lengthwise portion and a fourth axially facing lengthwise portion. In the extended portion of the drive ribbon defining a helix, the proximal edge section of the ribbon is engaged with an adjacent portion of the distal edge section with the second lengthwise portion of the proximal edge surface being engaged with the third lengthwise portion of the distal edge surface and wherein the first lengthwise portion of the proximal edge surface and the fourth lengthwise portion of the distal edge surface extend radially outwardly in opposite directions. A mechanical drive is operably coupled with the drive ribbon and selectively rotates the drive ribbon about the drive axis wherein rotation of the drive ribbon in a first direction extends the drive ribbon and rotation of the drive ribbon in an opposite second direction retracts the drive ribbon. A thrust member is operably disposed between the support structure and the drive ribbon. The thrust member is engaged with the first lengthwise portion of the proximal edge surface. A bearing member is supported on the drive ribbon proximate a distal end of the drive ribbon. The bearing member is adapted to transfer an axial force to the drive ribbon when the drive ribbon is extended.

In some embodiments, the fourth lengthwise portion of the distal edge surface projects radially outwardly and the first lengthwise portion of the proximal edge surface projects radially inwardly.

In some embodiments, the thrust member includes a helical thread engageable with the first lengthwise portion of the proximal surface. In such an embodiment, the helical thread may extend for greater than 360 degrees about the drive axis.

In an embodiment with a thrust member having a helical thread, the device may be configured such that the fourth lengthwise portion of the distal edge surface projects radially outwardly and the first lengthwise portion of the proximal edge surface projects radially inwardly and the delivery device further includes a ribbon bearing member circumscribing the drive ribbon wherein the ribbon bearing member defines a second helical thread engageable with the fourth lengthwise portion of the distal edge surface.

In such an embodiment having a second helical thread, the helical thread of the thrust member may extend for greater than 360 degrees about the drive axis. In still other embodiments, the second helical thread may extend for greater than 360 degrees about the drive axis with the ribbon bearing member circumscribing the drive ribbon proximate the thrust member.

In some embodiments, when the drive ribbon is unrolled and positioned in a plane, the drive ribbon defines an arc. In such an embodiment, the ribbon may be configured such that, when the drive ribbon is unrolled and positioned in a plane, the proximal edge section is positioned radially inward of the distal edge section and, when the ribbon defines a helix, the fourth lengthwise portion of the distal edge surface projects radially outwardly and the first lengthwise portion of the proximal edge surface projects radially inwardly.

In some embodiments, one of the proximal and distal edge sections define a plurality of pegs and the other one of the proximal and distal edge sections define a plurality of holes, wherein, in the extended part of the drive ribbon defining a helix, engagement of the proximal edge section of the ribbon with the adjacent portion of the distal edge section includes engagement of the pegs with the holes.

In an embodiment having pegs and holes, the drive ribbon may define a plurality of gear teeth engageable with the mechanical drive whereby the mechanical drive can engage and rotate the drive ribbon by transmitting a rotational force through the plurality of gear teeth. For example, the mechanical drive may include a worm gear engageable with the plurality of gear teeth.

In an embodiment wherein the ribbon includes pegs, holes and gear teeth, the drive ribbon may be configured such that it defines first and second major surfaces on opposing sides of the drive ribbon and the plurality of pegs, the plurality of holes and the gear teeth are all expressed on the first major surface of the drive ribbon whereby the plurality of pegs, the plurality of holes and the gear teeth are adapted to be machined from the side of the first major surface and wherein the second major surface defines a planar surface. In such an embodiment, the drive ribbon may be a unitary one-piece ribbon and all axial forces transferred between the bearing member and the thrust member when the drive ribbon is at least partially extended are transferred by the unitary one-piece ribbon and wherein the outermost portions of the first and second major surfaces define planes which are parallel with each other and the distance between the planes defined by the first and second major surfaces defines the greatest thickness of the drive ribbon.

In some embodiments, the delivery device may also include a bobbin that is rotatable relative to the thrust member with the retracted portion of the drive ribbon being stored in the bobbin.

It is noted that several different features of the delivery device are disclosed herein and these features may be combined in various different configurations. While several different combinations of such features are described herein, the person having ordinary skill in the art will realize that further such combinations not explicitly described herein are also possible and enabled by the present disclosure and are within the scope of the present application.

BRIEF DESCRIPTION OF THE DRAWINGS

The above mentioned and other features of this invention, and the manner of attaining them, will become more apparent and the invention itself will be better understood by reference to the following description of an embodiment of the invention taken in conjunction with the accompanying drawings, wherein:

FIG. 1A is a side view of a first embodiment of a delivery device.

FIG. 1B is an end view of the first embodiment.

FIG. 1C is another end view of the first embodiment.

FIG. 1D is side view of the first embodiment with the cap removed and a needle assembly attached.

FIG. 1E is an end view of the embodiment of FIG. 1D.

FIG. 1F is a perspective view of the first embodiment.

FIG. 2A is a side view of a prior art delivery device.

FIG. 2B is an end view of the prior art device.

FIG. 2C is another end view of the prior art device.

FIG. 2D is side view of the prior art device with the cap removed and a needle assembly attached.

FIG. 2E is an end view of the prior art device of FIG. 2D.

FIG. 2F is a perspective view of the prior art device.

FIG. 3A is a side view of a second embodiment of a delivery device.

FIG. 3B is an end view of the second embodiment.

FIG. 3C is another end view of the second embodiment.

FIG. 3D is side view of the second embodiment with the cap removed and a needle assembly attached.

FIG. 3E is an end view of the embodiment of FIG. 3D.

FIG. 3F is a perspective view of the second embodiment.

FIG. 4 is a partial schematic perspective view of the drive assembly.

FIG. 5 is a partial perspective view of the drive ribbon.

Figure 7:
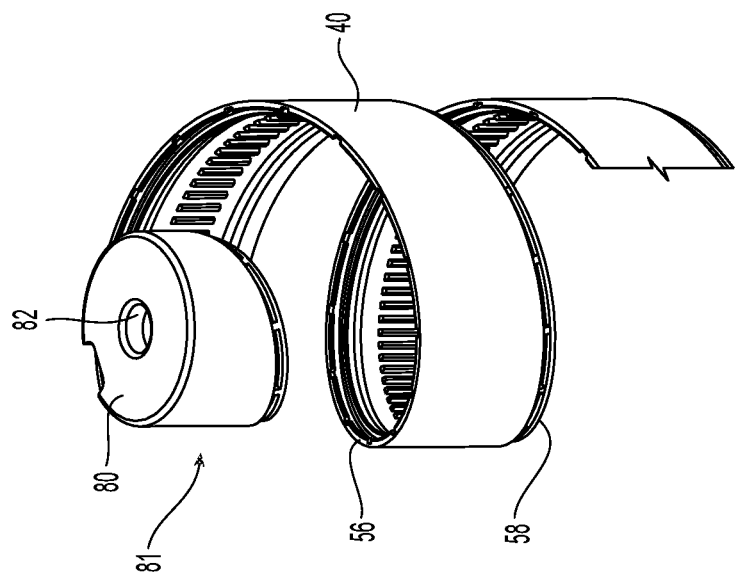
FIG. 7 is another partial perspective view of the drive ribbon.

Corresponding reference characters indicate corresponding parts throughout the several views. Although the exemplification set out herein illustrates an embodiment of the invention, in one form, the embodiment disclosed below is not intended to be exhaustive or to be construed as limiting the scope of the invention to the precise form disclosed.

DETAILED DESCRIPTION

A first embodiment of a compact medical delivery device 20 is shown in FIGS. 1A-1F while a second embodiment of a compact medical delivery device 20A is illustrated in FIGS. 3A-3F. One conventional prior art medical delivery device 21 is shown in FIGS. 2A-2F. The device 21 illustrated in FIGS. 2A-2F is a Kwikpen injector commercially available from Eli Lilly and Company which has headquarters in Indianapolis, Indiana and has a length of approximately 145 mm. As can be seen in a comparison of FIGS. 1A, 2A and 3A, the compact medical delivery devices 20, 20A are considerably shorter in length than the conventional device 21. The conventional device 21 is, however, thinner than compact devices 20, 20A as can be seen with reference to FIGS. 1B, 1C, 2B, 2C, 3B and 3C.

Figure 17:
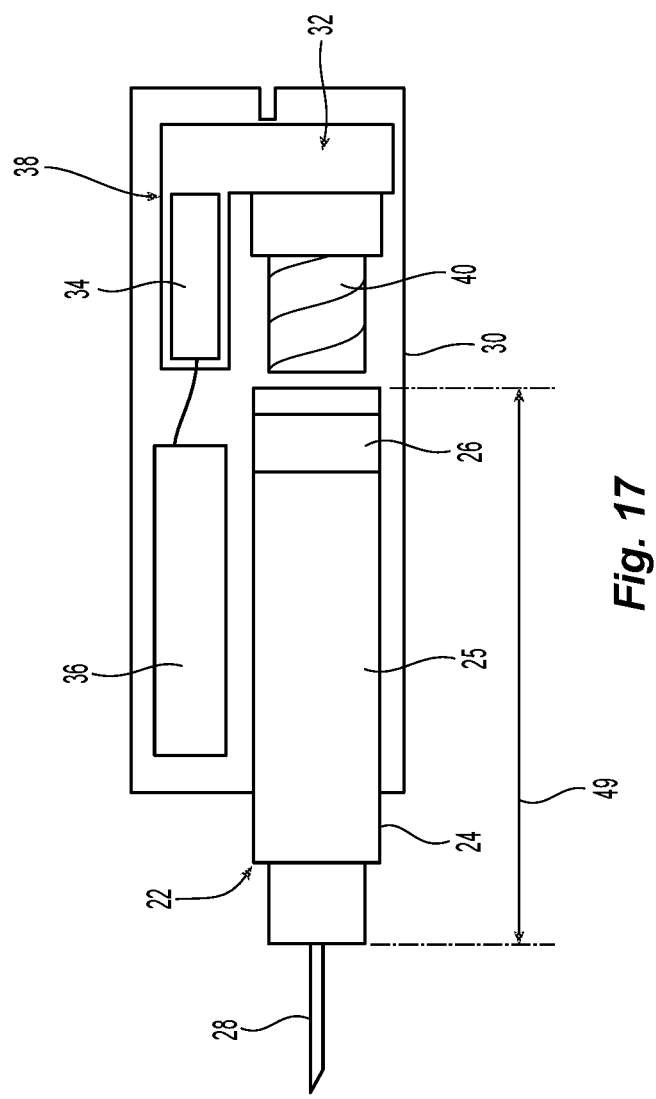
FIG. 17 is a schematic view of the first embodiment.

Medical delivery device 20 receives a medicament container 22. As schematically depicted in FIG. 17, medicament container 22 includes a container body 24 holding a medicament 25, for example, insulin, inside its cylindrical barrel. A piston 26 is disposed within body 24 and advancement of piston 26 within container body 24 expels medicament 25 through outlet 28. In the illustrated embodiment, outlet 28 is an injection needle having one end that pierces a septum of the container and an opposite end that can be inserted into a patient to inject the medicament 25.

Device 20 also includes a support structure 30 that is adapted to support medicament container 22. Support structure 30 also functions as a device housing in the illustrated embodiment and is also referred to herein as a housing. Housing 30 also supports a drive assembly 32 for advancing piston 26 and is adapted to be held in a human hand. Device 20 and device 20A are generally similar but do have different housings with housing 30A of device 20A being slightly larger than housing 30.

Both housings 30, 30A include a removable cap 31, 31A which are releasably securable to housings 30, 30A and cover outlet/needle 28 when the device is not being used. FIGS. 1D and 3D illustrate devices 20, 20A with caps 30, 30A removed while FIGS. 1A and 3A show caps 31, 31A installed on housings 30, 30A. As can be seen in FIGS. 1D and 3D, the caps 30, 30A are used to cover a standard needle that also has a removable, cylindrical inner needle shield 29.

As can be seen with reference to FIGS. 3A and 3D, removal of cap 31A exposes nearly the entire longitudinal length of container body 24. Generally, container body 24 will be formed out of glass or other transparent material. By exposing this length of container body 24, the user can visually determine the quantity of medicament 25 remaining in cartridge body 24. In contrast, housing 30 only exposes the end of medicament container 22 near outlet 28 and provides an open slot 42 in housing 30 to allow the user to visually determine the quantity of medicament 25 remaining in container body 24. A transparent material can be used to form a window instead of using an open slot 42 to allow for such visual inspection.

Housing 30 includes a control knob 44 for controlling the setting of a dosage, a button 45 for initiating an injection and an electronic display 46 located on the end of housing 30. For example, knob 44 can be rotated to set the injection dosage and central button 45 depressed to initiate the injection process. Housing 30A includes controls 44A and an electronic display 46A on the side of housing 30A. Controls 44A are used to set an injection dosage while control button 45A on the end of housing 30A is used to initiate the injection procedure. While the illustrated embodiments have actuators located on the end of the housing for initiating an injection other locations on the housing for such a feature may also be employed. For example, the thicker body of the housing relative to conventional pens may cause some people to grasp the device differently and an actuator which initiates the injection procedure may alternatively be deployed on the side of housing. The grip of the patient may also depend upon where on the patient's body the injection will occur and it may also be desirable in some embodiments to include multiple actuators on the housing to facilitate various gripping scenarios.

Medicament container 22 has a storage volume of at least 3 mL and is shown in the form of a conventional medicament cartridge. Support structure 30 may define an axial length of no more than 110 mm, or even an axial length of no more than 100 mm. The axial length of support structures 30, 30A are indicated by reference numbers 48, 48A respectively in FIGS. 1A and 3A. As evident from FIGS. 1A and 3A, the axial length of the support structure as referred to herein includes the removable caps. In the illustrated embodiments, the capped axial lengths 48, 48A are both 105 mm. In the illustrated embodiment, the axial length 48, 48A of devices 20, 20A is less than twice the axial length 49 of container 22 (not including needle 28). A standard 3 mL medicament cartridge used for insulin has an axial length of 64 mm and a plunger travel of approximately 43 mm.

It is the use of a drive assembly 32 having a drive ribbon 40 which allows devices 20, 20A to have relatively short axial lengths 48, 48A. FIG. 17 provides a schematic overall view of device 20 showing how container 22 is positioned in support structure 30 relative to drive assembly 32. Drive assembly 32 includes a mechanical drive 38 coupled with drive ribbon 40. Drive ribbon 40 is incrementally moveable between a retracted configuration and an extended configuration. With a medicament container 22 installed in device 20, the movement of drive ribbon from a retracted configuration to an extended configuration extends drive ribbon 40 and causes the advancement of piston 26 and the consequent discharge of medicament through outlet 28.

Selective rotation of drive ribbon 40 by mechanical drive 38 causes either the retraction or extension of drive ribbon 40. In the illustrated embodiment, mechanical drive 38 includes a DC electric motor 34 and a battery 36, e.g., a single AAA battery or rechargeable lithium ion cell, for powering motor 34. Alternative arrangement could employ an external electrical power source or an alternative form of torque supply. For example, a torque spring or other arrangement could be manually tensioned with the selective release of such tension providing the torque necessary to drive the operation of drive assembly 32.

Mechanical drive 38 is selectively coupled with the drive ribbon to rotate ribbon 40 about a drive axis 50 in either rotational direction. In a first rotational direction it causes drive ribbon 40 to extend axially, in the opposite second rotational direction it causes the retraction of drive ribbon 40. Rotation of drive ribbon 40 shifts the ribbon between spiral and helical configurations. When drive ribbon 40 is fully extended, the majority, if not all, of drive ribbon 40 will be in a helical configuration. When drive ribbon 40 is fully retracted, the majority, if not all, of drive ribbon 40 will be in a spiral configuration. In most axial positions, an extended portion 52 of drive ribbon 40 will define a helix while a retracted portion 54 of drive ribbon 40 will define a spiral. Rotation of drive ribbon 40 causes the ribbon to incrementally shift between the two configurations.

Figure 6:
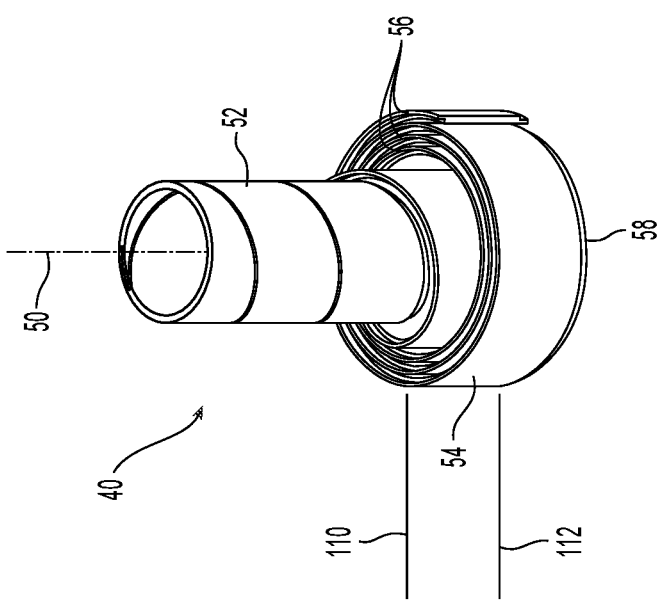
FIG. 6 is another perspective view of the drive ribbon.

FIGS. 5-11 provide detailed views of drive ribbon 40. FIG. 6 illustrates ribbon 40 in a configuration wherein ribbon 40 is partially extended. In FIG. 6, retracted portion 54 defines a spiral while extended portion 52 defines a helix. In retracted portion 54, the axial end surface of distal edge section 56 of ribbon 40 for each of the spiral wraps lie in a common plane 110, similarly, the axial end surface of proximal edge section 58 of each of the spiral wraps also lie in a common plane 112. This spiral arrangement allows the retracted portion 54 of ribbon 40 to be stored in a minimal axial space that is approximately equal to the width of ribbon 40. In the extended portion 52 of drive ribbon 40, proximal edge section 56 is directly bearingly engaged with an adjacent portion of the distal edge section 58.

Figure 11:
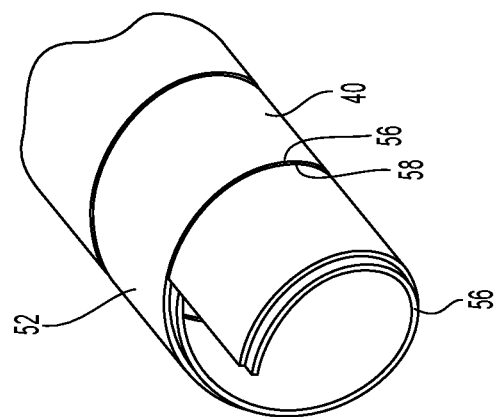
FIG. 11 is a schematic perspective view showing an extended portion of the drive ribbon.

It is noted that FIGS. 6 and 11 show helical extended portion 52 with engaged edges while FIGS. 5 and 7 show an exploded view of drive ribbon 40. FIGS. 5 and 7 are provided for purposes of explaining and showing the details of ribbon 40. In use, drive ribbon 40 would not assume the exploded configuration shown in FIGS. 5 and 7.

Figure 9:
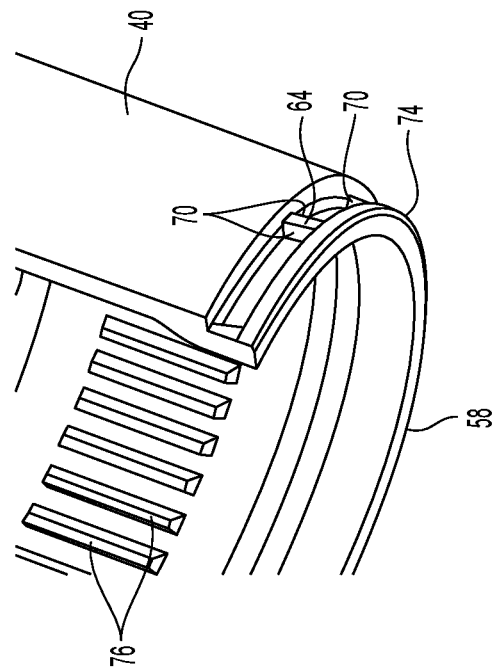
FIG. 9 is another detail partial perspective view of the drive ribbon.
Figure 8:
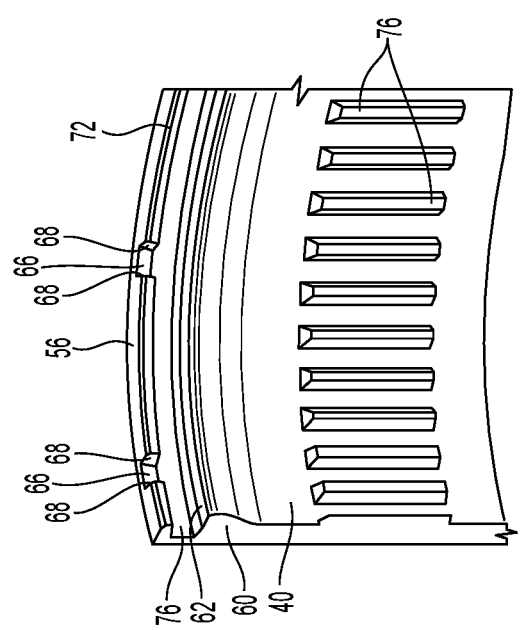
FIG. 8 is a detail partial perspective view of the drive ribbon.

One of the proximal 58 and distal 56 edge sections of ribbon 40 define a radially extending lip 60 to directly and bearing engage the other one of the proximal 58 and distal 56 edge sections. As can be seen in FIG. 8, in the illustrated embodiment, it is distal edge section 56 that includes a radially extending lip 60 and that the illustrated lip 60 extends radially inward. Lip 60 includes an axially facing surface 62 that is generally perpendicular to axis 50 which engages opposing proximal edge 58 to allow for the transfer of axially compressive forces. Ribbon 40 also provides for the transfer of torque forces. One of the proximal 58 and distal 56 edge sections of ribbon 40 defines a plurality of projections 64 with the other one of the proximal 58 and distal 56 edge sections defining a plurality of cooperating recesses 66. The interfitting of projections 64 with recesses 66 allow for the transfer of torque and help keep the proximal 58 and distal 56 edge sections interlocked as ribbon 40 is rotated. As can be seen in FIGS. 8 and 9, in the illustrated embodiment, it is distal edge section 56 that defines the plurality of recesses 66 and it is proximal edge section 58 that defines the plurality of projections 64. It is noted that it is the engagement of sidewall surfaces 68 of recesses 66 with sidewall surfaces 70 of projections 64 that allow for the transfer of torque. Sidewall surfaces 68 and 70 both define planar surfaces that are oriented substantially radially relative to axis 50. This radial orientation of the engaged sidewall surfaces resists shear forces along the joint and thus torsion in the column formed by the extended ribbon 40. Various other arrangements and configurations of the cooperating projections 64 and recesses 66 can be used. For example, recesses 66 could form openings that extend through the full thickness of ribbon 40. As a result of the resistance to shear forces along joint formed by the engaged edges, the resulting column carries torsional loads preventing one end from rotating relative to the opposite end. It also resists the twisting and uncoiling of the column formed by extended portion 52 of ribbon 40.

Distal 56 and proximal 58 edge sections also include radially extending flanges 72, 74 respectively. Flange 72 on distal edge section 56 extends radially inwardly while flange 74 on proximal edge section 58 extends radially outwardly. When the distal and proximal edge sections 56, 58 are engaged, radially outwardly extending flange 74 is seated in groove 76 defined by lip 60 and flange 72. Engagement of flanges 72, 74 provides resistance to axially acting tensile forces and prevents the engaged distal and proximal edge sections 56, 58 from axially separating when subjected to axially acting tensile forces.

When deployed the ribbon 40 is formed into a helix to form an interlocked rigid cylindrical column. Interlocking of the distal 56 and proximal 58 edge sections gives the column axial and torsional rigidity and strength as described above. The ribbon edge sections 56, 58 mechanically engage one another in a detachable and re-attachable manner. The deployment process, discussed below, is continuous, enabling a smooth and accurate injection process.

The column formed by extended portion 52 of ribbon 40 acts as a continuous tubular structure and will primarily carry compressive axial loads which correspond to the force necessary to expel medicament from container 22. It will also carry some torsional loads generated by the rotation of ribbon 40 as ribbon 40 is extended and retracted. Although no axial tensile loads are generally applied to ribbon 40, the use of interfitting flanges 72, 74 provides resistance to axial tensile loads and thereby prevents the engaged edges of ribbon 40 from axial separation during use and enhances the reliability of ribbon 40.

Figure 10:
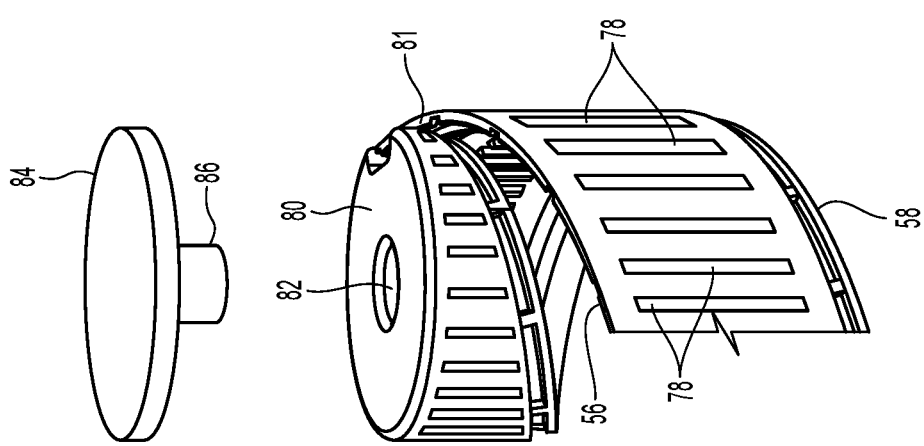
FIG. 10 is another detail partial perspective view of the drive ribbon.
Figure 13:
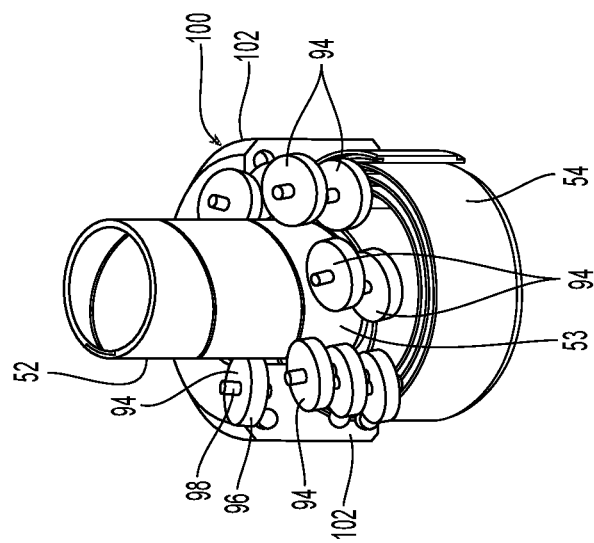
FIG. 13 is a schematic perspective view showing a ribbon bearing assembly around a drive ribbon.

Drive ribbon 40 also defines a plurality of gear teeth 76 that are engageable with mechanical drive 38 whereby mechanical drive 38 can rotate drive ribbon 40 by transmitting a rotational force through the plurality of gear teeth 76. As can be seen in FIGS. 8 and 9, gear teeth 76 are disposed on the radially inward facing surface of ribbon 40. While gear teeth 76 are disposed on the inner face of ribbon 40, an alternative arrangement may utilize gear teeth on the radially exterior surface of ribbon 40. FIG. 10 illustrates a set of gear teeth 78 on the exterior surface of ribbon 40 that are formed by a series of recesses. Either internal 76 or external 78 gear teeth can be used to rotate ribbon 40. Still other variations are also possible, for example, gear teeth could be employed on the proximal edge of ribbon 40 or both internal and external gear teeth could be employed on the same ribbon. Engagement and rotation of ribbon 40 by mechanical drive 38 is discussed in greater detail below.

The illustrated embodiments of drive ribbon 40 utilize a flexible polymeric ribbon that has been machined to define the various features of the ribbon. Nylon, polypropylene and high density polyethylene are examples of suitable polymeric materials that may be used to form ribbon 40. While the illustrated embodiments are machined, alternative embodiments could use a molding process to form a polymeric ribbon 40 with all of its edge features. It is envisioned that molding the ribbon in a flat arrangement and then rolling the ribbon into a spiral configuration will be the most efficient manufacturing method of forming a ribbon 40.

Other materials may also be used to form ribbon 40. For example, thin metal strip could be used to form ribbon 40. Photo etching, laser etching or other suitable micro machining methods could be used to form the individual features of ribbon 40. Alternatively, a metal ribbon could be formed by diffusion bonding two half-thickness layers instead of using a single metal strip.

Still other ribbon embodiments might take the form of an overmolded metal strip. The metal strip would be provided with the distal edge features and the overmolded plastic portion of the ribbon would form the proximal edge features. This approach combines the desirable stiffness, elasticity and creep resistance of metal with the low friction and manufacturing ease of forming small features in molded plastic. For all embodiments of ribbon 40, it is desirable for ribbon 40 to be flexible so that ribbon 40 can be extended and retracted, and undergo concomitant elastic strains, without permanent deformation.

The distal end of ribbon 40 must exert axial forces on piston 26. To enable such a transfer of force, a bearing member 80 is supported on drive ribbon 40 proximate distal end 81 of drive ribbon 40 and is adapted to exert an axial force on piston 26. The column formed by ribbon 40 will rotate as it extends, however, piston 26 of container 22 does not rotate. A rotational bearing 82 is provided at the distal end 81 of ribbon 40 to account for the relative rotational motion and allow relative rotational movement between drive ribbon 40 and piston 26 about drive axis 50. In the illustrated embodiment, rotational bearing 82 is a jewel bearing located on bearing member 80. In the illustrated embodiment, bearing member 80 is shown as an integral part of drive ribbon 40, but the two can also be separate parts with a suitable joint therebetween. As can be seen in FIG. 10, a transfer member 84 acts on piston 26 or other intermediate part and includes a projecting member 86 that rotates within jewel bearing 82. Transfer member 84 pushes against and advances piston 26 and does not rotate relative to piston 26 as ribbon 40 is advanced. As ribbon 40 advances and ribbon 40 rotates relative to piston 26, projecting member 86 rotates within rotational bearing 82. Since loads are predominantly axial and minimizing frictional losses is desirable, the revolute joint at this location may be a low-friction jewel bearing, however, other arrangements allowing for relative rotation of ribbon 40 and piston 26 may also be used.

Figure 12:
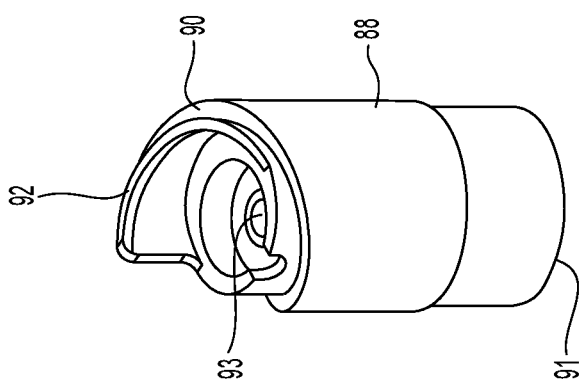
FIG. 12 is a perspective view of a ribbon thrust member.

A thrust member 88 (FIG. 12) is operably disposed between support structure 30 and drive ribbon 40. Thrust member 88 is engaged with a portion of proximal edge 58 of ribbon 40 when drive ribbon 40 is at least partially extended. More specifically, thrust member 88 engages ribbon 40 where ribbon 40 transitions between a spiral configuration and a helical configuration and also bears axial compressive forces acting on ribbon 40. In the illustrated embodiment, drive ribbon 40 is a one-piece unitary ribbon and all axial forces transferred between bearing member 80 and thrust member 88 when the drive ribbon 40 is at least partially extended are transferred by the unitary one-piece ribbon 40. The axial compressive load created by bearing on piston 26 is transmitted to the support structure 30 through bearing surface 91 on the axial end of thrust member 88 opposite ramp 90. In this regard, it is noted that some of the axial compressive force acting on ribbon 40 will act on the medicament in container 22 causing the ejection of the medicament through outlet 28.

Figure 18:
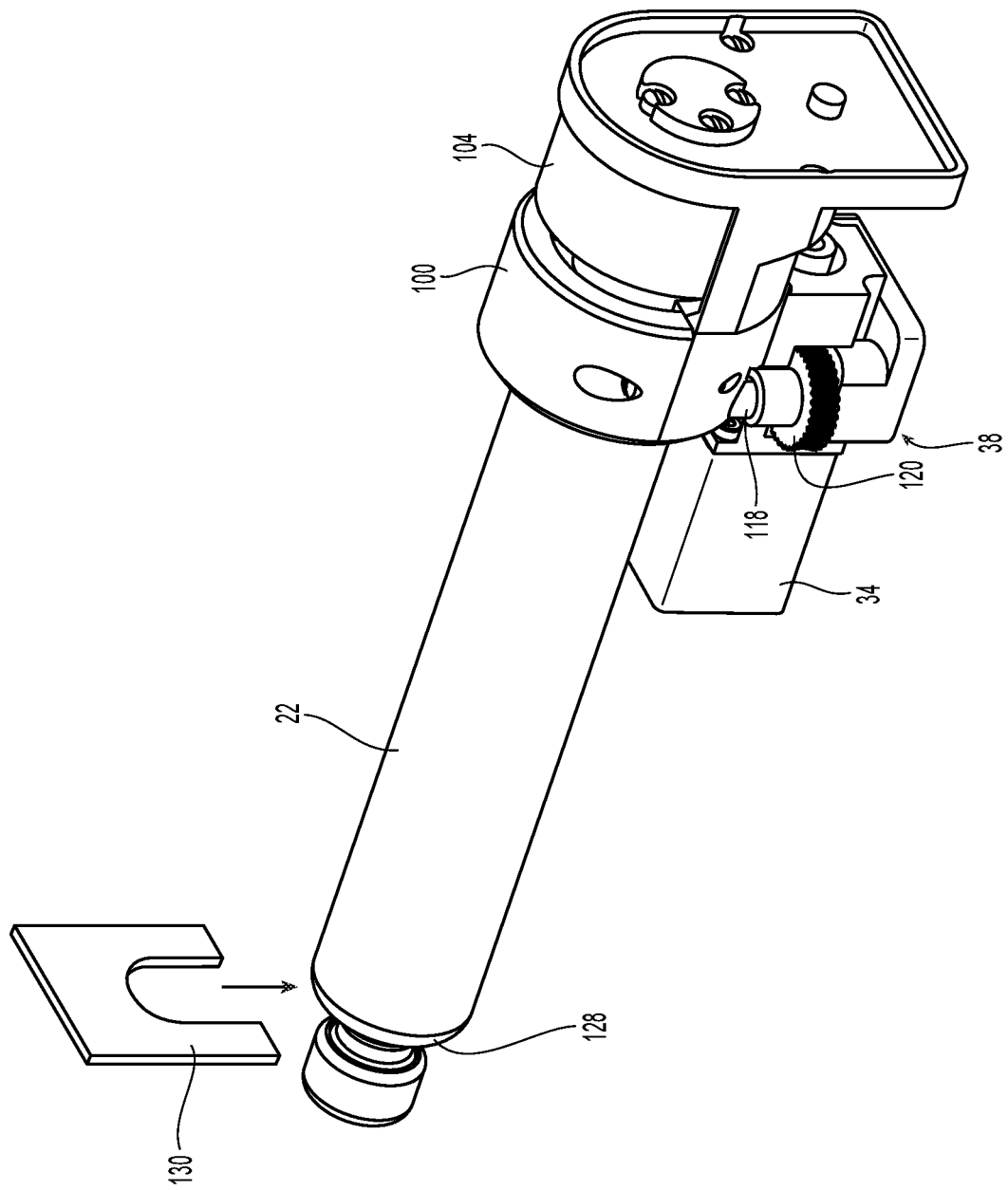
FIG. 18 is partial perspective view showing the drive assembly and a medicament container.
Figure 19:
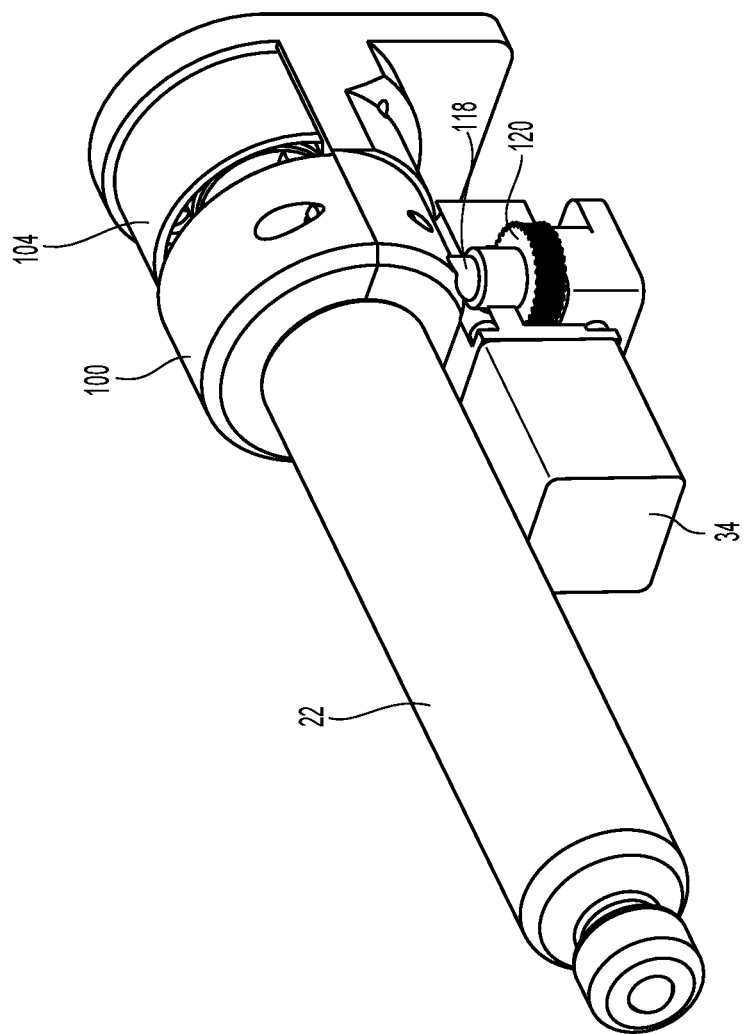
FIG. 19 is another partial perspective view showing the drive assembly and a medicament container.
Figure 20:
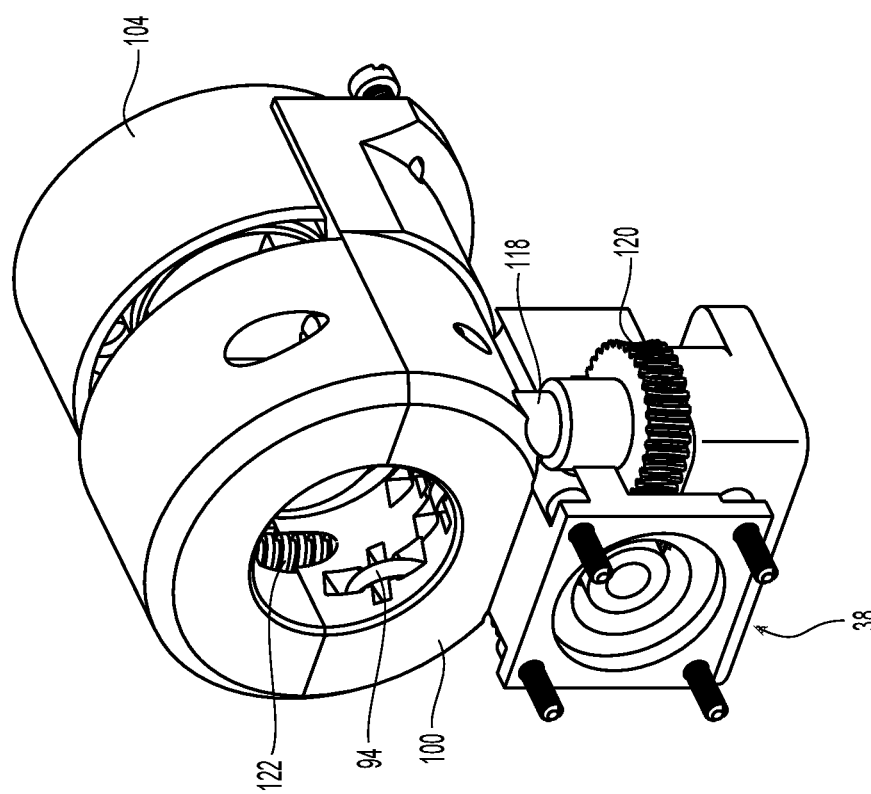
FIG. 20 is a partial perspective view of the drive assembly.

It is also noted that the axial force exerted by the transfer member 84 on piston 26 is at least partially transmitted to support structure 30 through the medicament container 22 otherwise, container 22 would simply move axially together with ribbon 40 as ribbon 40 was extended. If container 22 is held within device 20, 20A by a friction fit within support structure 30, this friction fit may be sufficient to hold container 22 in place and absorb the axially compressive forces acting on container. Alternatively, a structural retainer could be used to retain container 22 in support structure 30. FIG. 18 schematically depicts how shoulder surface 128 of container 22 could be engaged by sliding a retainer with bearing surface 130 into engagement with shoulder 128. Compressive forces would be transferred from shoulder 128 to surface 130 and, thus, to the retainer which is a part of support structure 30.

Thrust member 88 is rotationally fixed relative to housing 30 and defines a helical ramp 90 that engages proximal edge 58 of ribbon 40. Compressive axial forces are transferred between ribbon 40 and thrust member 88 at helical ramp 90. Helical ramp 90 also guides the transition of ribbon 40 between its spiral and helical configurations.

When the drive ribbon is rotated in a first direction so that the proximal edge 58 engaged with ramp 90 is sliding upward and in a distal direction, a transition portion 53 of ribbon 40 that is engaged with helical ramp 90 is guided by ramp 90 into a helical arrangement and is transitioned from the retracted (spiral) configuration 54 to the extended (helical) configuration 52. Similarly, when ribbon 40 is rotated in a second, opposite, direction, transition portion 53 of the ribbon 40 engaging the helical ramp 90 slides down ramp 90 and transitions from the extended (helical) configuration 52 to the retracted (spiral) configuration 54.

Due to the limited area of contact between proximal edge section 58 and ramp 90, the friction resisting sliding movement is relatively small. To further limit frictional resistance to sliding along ramp 90, thrust member 88 may be formed out of a lubricious polymeric material such as acetal. Proximal edge section 58 may form a continuous surface and avoid recesses or interruptions in the portion of proximal edge section 58 that engages ramp 90 to avoid the increased resistance and greater wear that such irregular surfaces are likely to cause.

Alternative thrust support surfaces may also be used. For example, instead of using a sliding surface, small rollers could be arranged in helical pattern along the outer perimeter of the thrust member. Due to the small scale and small forces generally anticipated when using ribbon 40 to inject a medicament, the greater manufacturing difficulties and expense that such rollers would require will generally not be warranted.

An axially extending wall 92 is located on the radially inner edge of helical ramp 90 and extends in the distal direction. Wall 92 prevents proximal edge section 58 from being biased radially inward out of engagement with ramp 90 by ribbon bearing member 100. Ribbon bearing member 100 circumscribes thrust member 88 and exerts a radially inward bearing force on drive ribbon 40 proximate helical ramp 90. Ribbon bearing member 100 includes a sleeve 102 that surrounds thrust member 88 and a plurality of rollers 94 mounted within sleeve 102. Rollers 94 are engageable with drive ribbon 40 and exert a radially inward force and bias drive ribbon 40 onto helical ramp 90 as drive ribbon 40 is rotated. Rollers 94 include a cylindrical disk 96 which engages ribbon 40 and axle stubs 98 extending from opposite sides of disk 96 which are rotatably mounted on the inner surface of sleeve 102.

Figure 16:
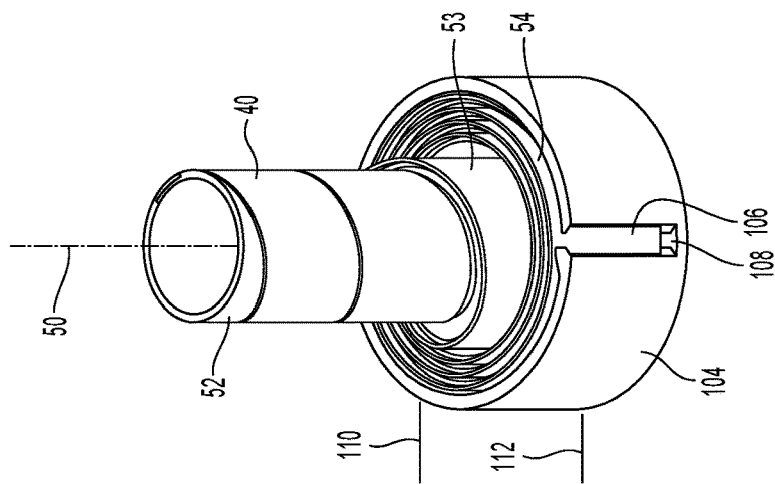
FIG. 16 is a schematic perspective view of a drive ribbon and a storage bobbin.

Ribbon 40 is fed onto helical ramp 90 from the retracted portion 54 of ribbon 40 which is stored within bobbin 104 in a spiral configuration as can be seen in FIG. 16. The proximal end 106 of ribbon 40 is secured to bobbin 104 and as ribbon 40 is rotated, bobbin 104 rotates with ribbon 40. In the illustrated embodiment, bobbin 104 is a cylindrical storage bobbin and is rotatably mounted on thrust member 88. In the illustrated embodiment, bobbin 104 includes an axially extending slot 108 in which proximal end 106 of ribbon 40 is secured. Various other methods may also be used to secure proximal end 106 to bobbin 104. Both ribbon 40 and bobbin 106 rotate about axis 50.

As can be seen in FIG. 16, for the retracted portion 54 of drive ribbon 40 disposed within bobbin 104, the axial end surface of distal edge section 56 of drive ribbon 40 lies in a first plane 110 oriented perpendicular to drive axis 50 and the axial end surface of proximal edge section 58 of drive ribbon 40 lies in a second plane 112 oriented perpendicular to drive axis 50. This spiral configuration allows ribbon 40 to be stored in a minimal amount of space and is particularly useful for reducing the axial length of the storage space required to store ribbon 40. The distance between planes 110, 112 is equivalent to the width of ribbon 40, i.e., the shortest distance between the opposing axial end surfaces defined by distal and proximal edge sections 56, 58 of ribbon 40.

As can also be seen in FIG. 16, the retracted portion 54 of ribbon 40 fills storage bobbin 104 from the radially outermost location within bobbin 104 inwardly with the inner-most portions of the stored ribbon 40 still defining a larger radius than the radius of helical ramp 90. This facilitates the movement of ribbon 40 from the stored spiral configuration of retracted portion 54 to the extended helical configuration of extended portion 52 by engagement of ribbon 40 with ribbon bearing member 100.

It is desirable for ribbon 40 to naturally assume a coiled shape having a radius larger than the inner diameter of bobbin 104 so that ribbon 40 will expand to engage the inner surface of bobbin 104 when it is stored therein. Some plastic materials tend to creep and take on their stored dimensions. The use of a metal ribbon or an overmolded metal ribbon will minimize the risk of having the ribbon fail to expand and fill the radially outermost portions of bobbin 104.

While the illustrated embodiment utilizes a cylindrical storage bobbin 104 for ribbon 40, alternative embodiments are also possible. For example, a plurality of abutments within housing 30 may be sufficient for some embodiments, or, if ribbon 40 has the appropriate physical properties, it might naturally assume a spiral configuration when disengaged from an adjacent turn of the ribbon and thereby avoiding the use of a storage bobbin.

The size of storage bobbin 104 is chosen so that it will be adequate when ribbon 40 is fully retracted. When fully retracted, ribbon 40 has a minimum radius that is larger than the radius of ramp 90 which corresponds to the radius of the helical extended portion 52 of ribbon 40. When ribbon 40 is rotated in a direction that feeds stored ribbon 40 from storage bobbin 104 onto helical ramp 90, each additional coil of the ribbon transitions from the inside of the storage spiral onto the column formed by extended portion 52. The transition portion 53 of ribbon 40 gets radially smaller as it moves from its stored configuration in bobbin 104 onto ramp 90 and it becomes tangent to the helical column formed by extended portion 52 at the point where the ribbon 40 joins the helical column of extended portion 52. As the ribbon is moved radially inward along this helical path, the features along the distal edge section 56 of the transition portion 53 of ribbon 40 engage the features of the proximal edge section 58 of the lowermost turn of the extended portion 52 of ribbon 40.

The position where the radial lay-in and ribbon edge engagement occurs remains fixed within the device and fixed relative to thrust member 88. Distally from this point of engagement the ribbon is a helical column forming the extended portion 52; proximally from this point of engagement the ribbon relaxes through the transition helical spiral (transition portion 53), into the spiral arrangement (retracted portion 54) contained within storage bobbin 104.

All of the coils of ribbon 40 distal of the engagement location, i.e., the extended portion 52 of ribbon 40, are kept engaged with each other by the ribbon coil proximally below them. At the point of engagement, the proximal edge of the ribbon coil being engaged is still un-engaged and is biased radially inward by ribbon bearing member 100 so that the ribbon coil being engaged does not expand radially outward and fail to engage. At the same time, ribbon 40 must be maintained in a position encircling axis 50. These tasks are accomplished by external bearing 100 which surrounds roughly one full helical coil of ribbon 40. Relative to this fixed bearing 100, ribbon 40 both rotates and translates as ribbon 40 advances (or retracts) along its helical path.

As discussed above, the illustrated embodiment utilizes a ribbon bearing member 100 that includes a plurality of rollers 94. In this arrangement, each of the rollers 94 is tangent to the cylinder defined by ribbon 40 and tilted at the helix angle. Rollers 94 roll rather than slide along the cylinder defined by ribbon 40. The position of the rollers 94 establish and then maintain the engagement of the ribbon edge sections 56, 58 while keeping the overall helical structure of the engaged ribbon edges supported both radially and axially. While the disclosed rollers 94 are effective, alternative arrangements that are simpler and which can be more cost-effectively manufactured may be suitable for some applications. For example, small ball bearings disposed in a groove similar to a conventional ball bearing or that found in a ball screw may be suitable for some applications. A simple bushing formed out of a lubricious polymeric material may also be adequate for some applications.

Figure 15:
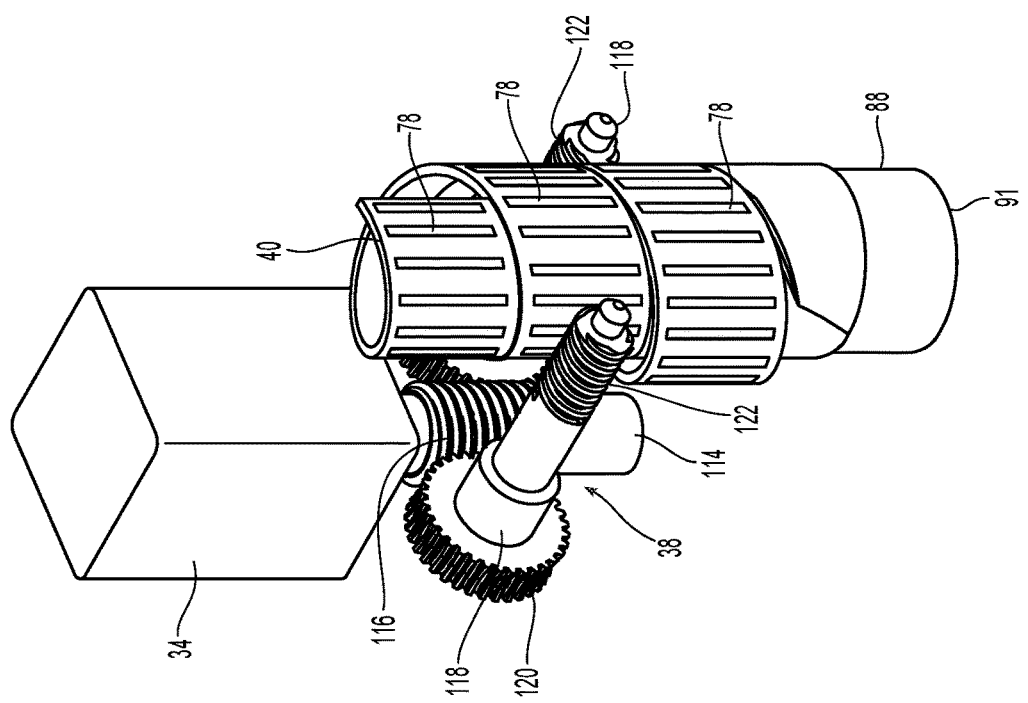
FIG. 15 is a schematic perspective view of an alternative mechanical drive assembly.
Figure 14:
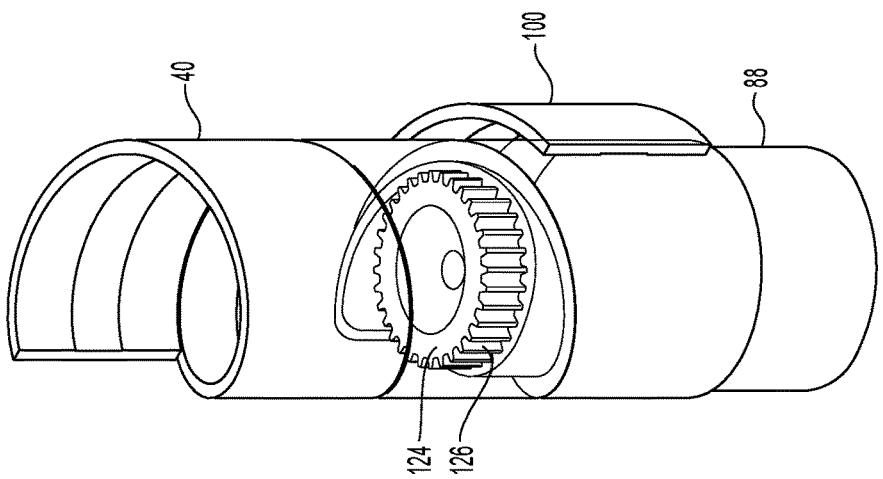
FIG. 14 is a schematic perspective view showing a mechanical drive assembly for engaging the drive ribbon.

FIG. 4 provides a partially transparent view of drive assembly 32 and views of alternate drive assemblies are provided in FIGS. 14 and 15. In the illustrated embodiments, drive assembly 32 includes a battery powered electrical motor 34 and a mechanical drive 38. Mechanical drive 38 includes motor shaft 114 which is driven by motor 34 and includes a gearing arrangement 116 for transferring torque generated by motor 34. The transfer of torque from motor 34 to ribbon 40 allows ribbon 40 to perform mechanical work, i.e., forcibly rotate and advance ribbon 40 to thereby advance piston 26, or, when rotated in the opposite direction, retract ribbon 40 and wind it into a spiral in bobbin 104.

Small electrical motor 34 provides the power to operate the extension and retraction of ribbon 40. Typically, motors of this size utilize a mechanical gear reduction. Motor shaft angle sensing can be used to control advancement of ribbon 40 and thus the dose delivered.

FIGS. 14 and 15 illustrate two different arrangements by which torque may be transferred from motor 34 to ribbon 40. Various other torque transfer arrangements and modifications to the illustrated arrangements may also be employed with drive ribbon 40.

In the embodiment of FIG. 14, ribbon 40 includes gear teeth 76 on the interior surface of ribbon 40. A gear member 124 having gear teeth 126 that meshes with gear teeth 76 is used to rotate ribbon 40. Gear member 124 includes a shaft (not shown) extending through opening 93 in thrust member 88. The shaft includes another gear arrangement that meshes with a transfer gear member which is also engaged with gearing arrangement 116 on motor shaft 114 whereby torque from motor 34 is transferred to ribbon 40.

In the internal gear drive arrangement depicted in FIG. 14, teeth 76 on the inner wall of ribbon 40 engage a gear inside the helical column formed by extended portion 52. As gear 124 rotates it causes ribbon 40 to rotate and either extend or retract. In the illustrated embodiment, the rotational axis of gear 124 is parallel to axis 50 and slightly offset. This offset arrangement together with gear 124 having an outside diameter less than the inner diameter of ribbon 40 at the location of gear 124 allows gear 124 to engage ribbon 40 at one location only instead of along the entire perimeter of gear 124. Gear teeth pitches are selected to establish conventional meshed engagement. With a straight-toothed gear, the internal teeth 76 on ribbon 40 are tilted by the helix angle (relative to the ribbon edge) to ensure correct meshing. Since ribbon 40 is extending (or retracting) as it rotates, the gear teeth slide axially along one another as ribbon 40 is rotated.

Drive gear 124 can also have helical teeth if the helical teeth are tilted to match the helix angle of extended portion 52. In such an application, ribbon teeth 76 can be perpendicular to the ribbon edge. Other relative angles between gear teeth 76 and ribbon edges 56, 58 are also possible. Various other arrangements are also possible, for example, alternative axis orientations are possible (for example, the gear could be arranged to be tangent to the helix).

The use of an internally positioned gear can be effective. For some applications, however, it does pose drawbacks. For example, it will generally require that some mechanical elements such as a gear train to rotate internal gear 124 be disposed at the proximal axial end of thrust member 88. This can add additional axial length to the overall device. This arrangement also requires that a sufficiently radially rigid mechanical structure hold the external ribbon bearing member 100 in place.

FIG. 15 illustrates an embodiment wherein ribbon 40 includes a gearing arrangement 78 on the exterior surface of ribbon 40. In this embodiment, two transfer gear members 118 transfer torque from motor shaft 114 to ribbon 40. More specifically, transfer gear members 118 each include a first gearing arrangement 120 that engages with gear arrangement 116 on shaft 114 and a worm gear 122 engaged with ribbon 40.

The external drive system shown in FIG. 15 uses a worm gear 122 enmeshed with external-facing slots 78 on ribbon 40. The worm 122 may be chosen to have a helix angle that matches the helix angle of extended portion 52 of ribbon 40 to thereby allow the slots 78 cut into ribbon 40 to be arranged perpendicular to the ribbon edge. Although two worm gears 122 are shown in FIG. 15, a single worm gear 122 could alternatively be used. As the worm(s) rotate they advance or retract the ribbon.

The use of an external worm drive such as transfer gear members 118 places the transfer gear member 118 on the side of ribbon 40 and therefore adds no axial length to the device. Additionally, transfer gear members 118 can reduce the number of rollers 94 because transfer gear members 118 provide radial support to ribbon 40.

The illustrated container 22 is a replaceable cartridge. To facilitate the convenient replacement of container 22 upon its depletion, a cartridge retainer may be used. Such retainers are well known in the art and typically utilize a threaded joint or bayonet joint, however, other suitable mechanical retention devices may also be used.

Another consideration regarding the replacement of container 22 is avoidance of user contact with extension portion 52 of ribbon 40. While contact with extension portion 52 will not necessarily cause damage, rough handling of ribbon 40 has the potential to impair the operability of ribbon 40, e.g., disengaging edge sections 56, 58 of extended portion 52. Various approaches can be used to inhibit or prevent such contact. For example, if the full length of extended portion 52 would be exposed upon removal of container 22, a mechanical interlock can be provided so that ribbon 40 is retracted prior to removal of container 22. If only the distal end of container 22 is exposed and extended portion 52 is shielded from contact by housing 30, an electrical interlock can command retraction of ribbon 40 when removal of container 22 is detected.

It is also noted that while the illustrated embodiments discussed herein utilize replaceable containers 22 to allow for the re-use of devices 20 and 20A-20C alternative embodiments could take the form of prefilled disposable devices or use a medicament container that is re-filled instead of discarded and replaced.

Figure 21:
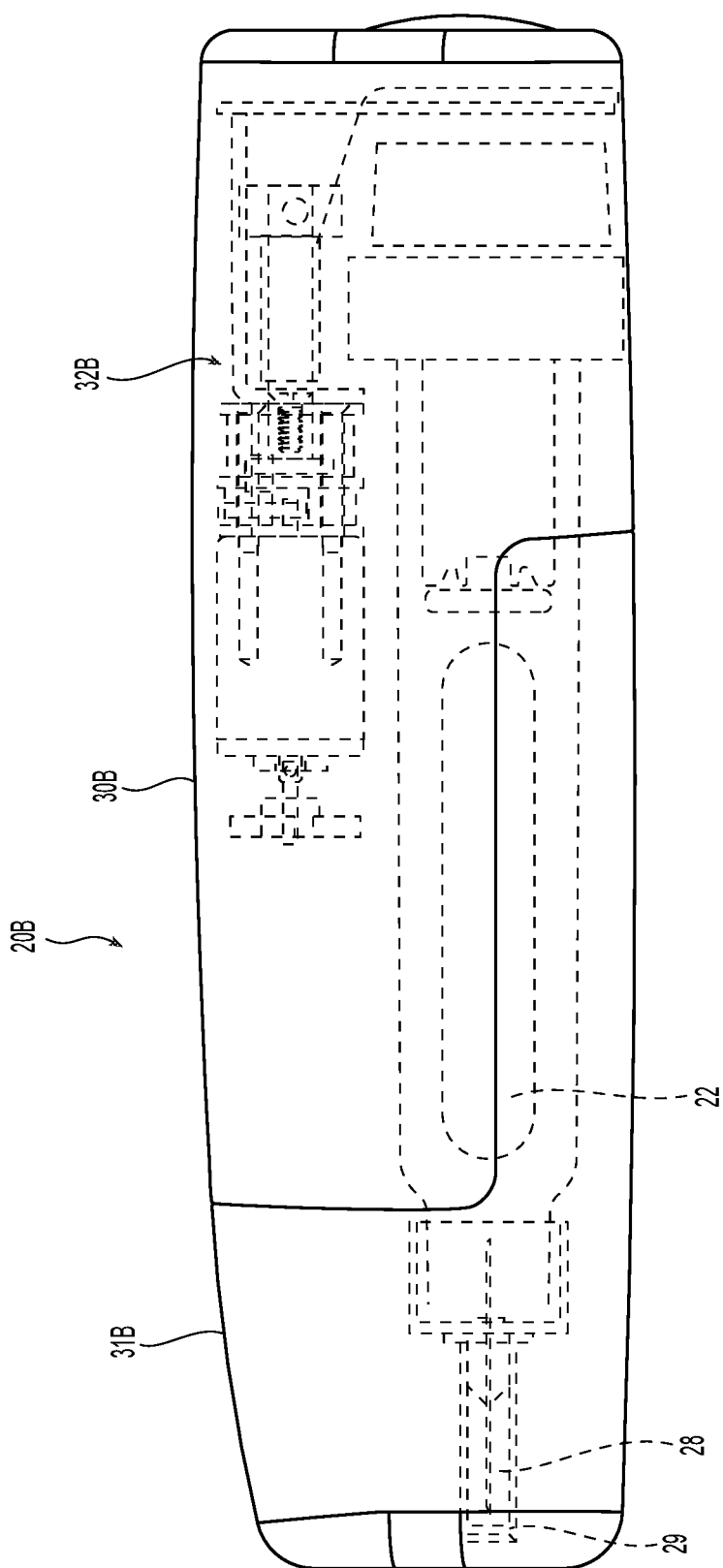
FIG. 21 is a side view of another embodiment.
Figure 33:
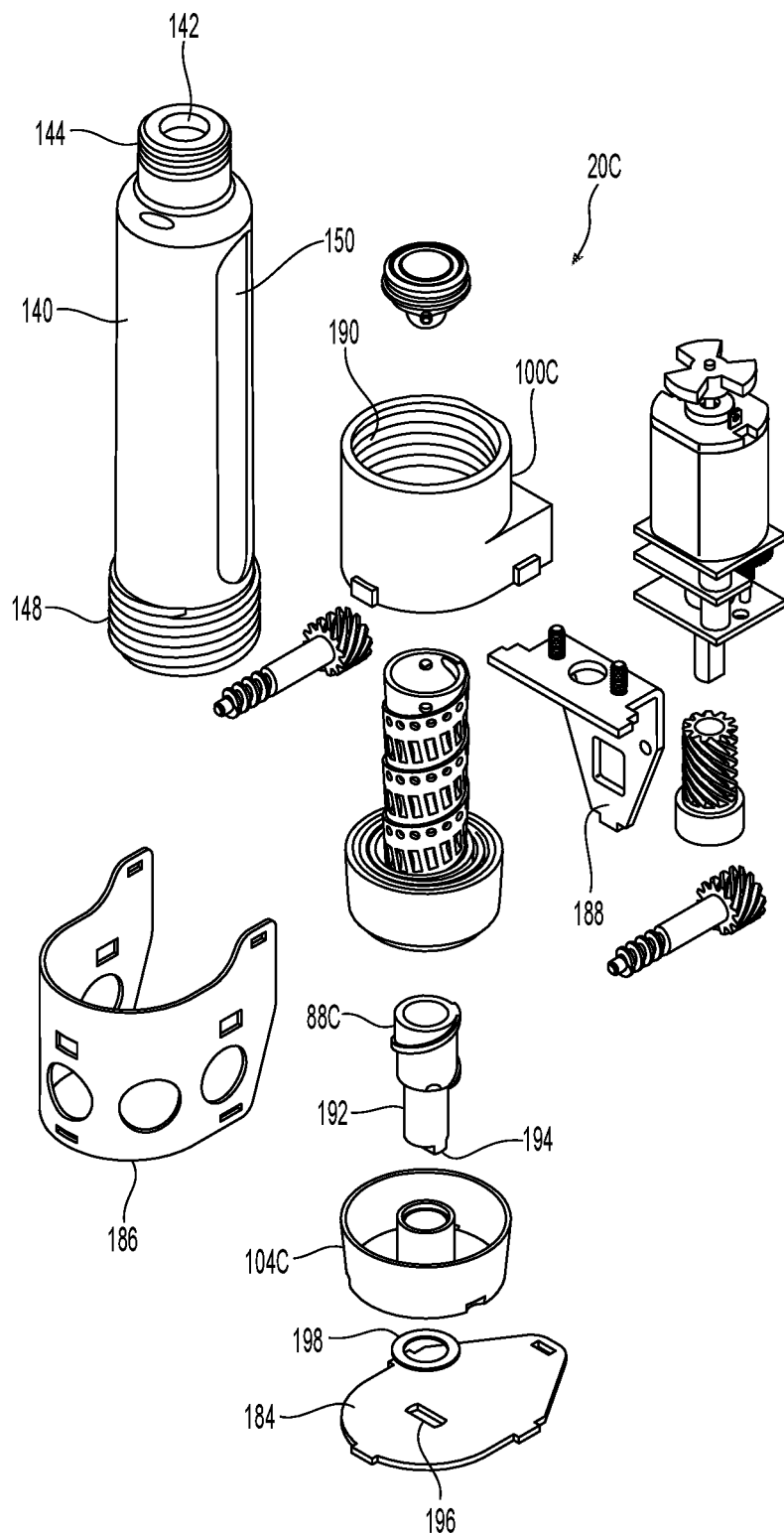
FIG. 33 is an exploded view of the embodiment of FIG. 30 without the housing.

Another embodiment, device 20B, is shown in FIGS. 21-29. Device 20B is generally similar to devices 20, 20A but has several modifications. The overall length of device 20B as shown in FIG. 21 is less than 110 mm. Device 20B dispenses medicament from a container 22 having a needle 28. A removable cap 31B covers needle 28 when device 20B is not in use and has sufficient space to allow for the use of an inner needle shield 29. Support structure 30B provides a housing for drive assembly 32B. A cartridge sleeve 140 receives container 22 and has an opening 142 through which needle 28 can be extended. Cartridge sleeve 140 is best seen in FIG. 33 and includes a threaded portion 144 adjacent opening 142. A securement cap 146 engages threaded portion 144 and is used to secure needle 28 to cartridge sleeve 140. A set of rear threads 148 secures cartridge sleeve 140 to the device. In the illustrated embodiments, rear threads 148 engage corresponding threads on an extension of the ribbon bearing member. The illustrated cartridge sleeve 140 also includes an axially extending opening 150 that functions as a window allowing a user to view the container 22 to see the quantity of medicament remaining therein without having to remove container 22. Cartridge sleeve 140 also provides a bearing surface which functions the same as surface 130 and may be formed by an internal shoulder contacting the narrowing portion of container 22. Various other means for securing container 22 within the device may alternatively be used.

Figure 22:
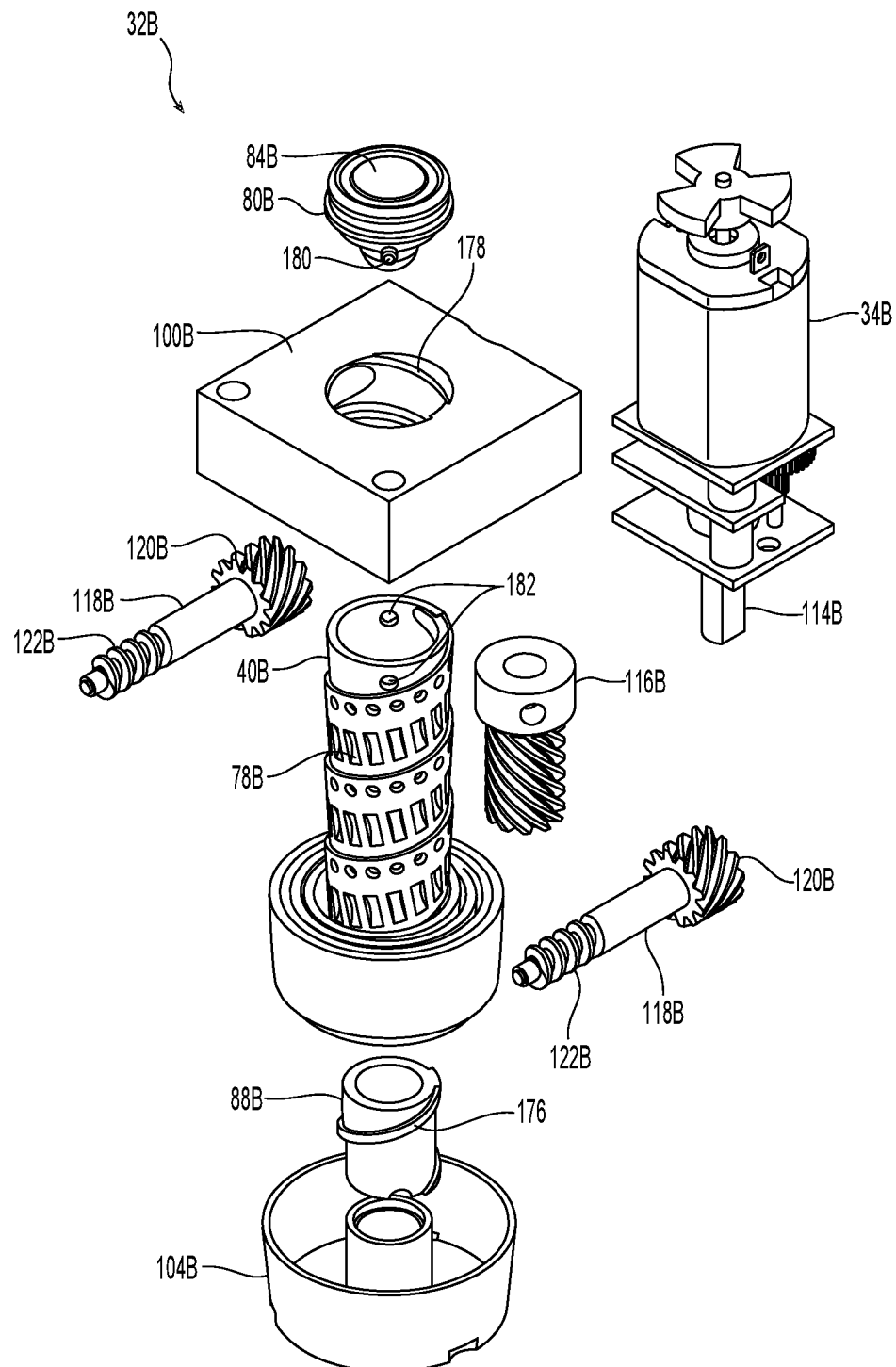
FIG. 22 is a partial exploded view of the embodiment of FIG. 21.
Figure 23:
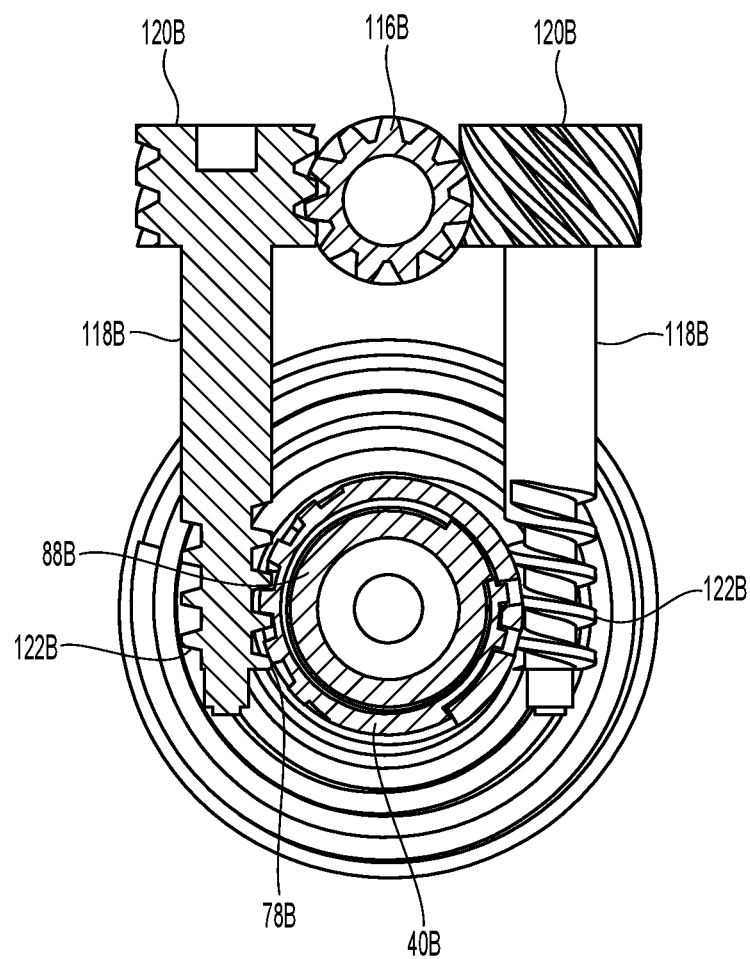
FIG. 23 is a cross sectional view taken along line 23-23 of FIG. 26.

FIG. 22 illustrates the main components of drive assembly 32B. Drive assembly 32B includes a DC motor 34B having an output shaft 114B on which a first gear 116B is secured. Gear member 116B engages gear members 120B located on two transfer gears 118B. Gear members 116B, 120B are cross axis involute helical gears. Worm gears 122B on transfer gears 118B engage gear teeth 78B on the exterior of drive ribbon 40B to rotatably drive ribbon 40B.

The worm gear pitch, gear ratio and pitch of gear slots 78B in ribbon 40B are all selected to work together. In this regard, it is noted that the selection of an integer number of ribbon teeth per half turn of the extended ribbon is a significant factor in determining appropriate values for these pitches and gear ratios.

Drive ribbon 40B differs from the drive ribbon of devices 20, 20A. Drive ribbon 40B includes a recessed area 152 along the proximal edge section 58B of ribbon 40B that receives an adjacent portion of the distal edge section 56B of ribbon 40B when ribbon 40B is extended and forms a helix. Recessed portion 152 does not, however, receive the full thickness of distal edge section 56B and a portion of both the distal and proximal edge sections project radially in opposite directions as a result.

A plurality of pegs 154 are located in recess 152 and engage a corresponding plurality of holes 156. In the illustrated embodiment, pegs 154 are located on the proximal edge section 58B with holes 156 being located on the distal edge section 56B. These positions, however, could be reversed. As drive ribbon 40B is extended and formed into a helix, the engagement of proximal edge section 58B with an adjacent portion of distal edge section 56B includes the engagement of pegs 154 with holes 156. In the illustrated embodiment, pegs 154 have a chamfered surface 155 that facilitates the entry and removal of pegs 154 from holes 156.

The engagement of pegs 154 with holes 156 secures the adjacent portions of drive ribbon 40B together axially. The engagement of pegs 154 and holes 156 also provides for the transfer of torque between adjacent portions of the extended ribbon and maintains the stability of the column formed by the extended ribbon.

In the illustrated embodiment, drive ribbon 40B has a first major surface 158 and a second major surface 160 on the opposite side of drive ribbon 40B. A plurality of gear teeth 78B are formed in first major surface 158. Gear teeth 78B are engaged by gear members 122B whereby drive assembly 32B can rotate drive ribbon 40B by transmitting a rotational force to drive ribbon 40B.

The configuration of drive ribbon 40B may take on a variety of different forms. In the illustrated embodiment, the plurality of pegs 154, recess 152, plurality of holes 156 and gear teeth 78B are all expressed on the first major surface 158. In this regard, it is noted that it is the opening of holes 156 on the second major surface 160 that receives pegs 154. While it is not necessary for the proper functioning of holes 156 for holes 156 to extend all the way to the first major surface 158, by extending holes 156 to the first major surface the manufacture of ribbon 40B is facilitated. More specifically, it allows for the manufacture of a flat ribbon having two flat planar surfaces and a subsequent machining or milling operation that forms the plurality of pegs 154, recess 152, plurality of holes 156 and gear teeth 78B to be performed from the side of the first major surface 158 and without requiring any such operation to be performed on the second major surface 160 forming the opposite side of ribbon 40B. This reduces the handling of ribbon 40B during manufacture and thereby improves efficiency and reduces cost. Ribbon 40B may be formed out of ABS (acrylonitrile butadiene styrene) or other suitable material. For example, while ABS is a relatively flexible material, other relatively stiffer material such as polycarbonate and metal ribbons may alternatively be used. When employing a relatively stiff material, it may be advantageous to use a plurality of perforations along the length of the ribbon to enhance the flexibility of the ribbon.

Prior to machining these features in ribbon 40B, it is a flat ribbon having two planar surfaces which are parallel to each other and without any features formed in the planar surface. As a result, after forming pegs 154, recess 152, holes 156 and gear teeth slots 78B, the outermost portions of the first and second major surfaces 158, 160 define planes 159, 161 which are parallel with each other and the distance 162 between these two planes 159, 161 defined by the first and second major surfaces defines the greatest thickness of drive ribbon 40B.

As mentioned above, the proximal edge section 58B of drive ribbon 40B includes a recess 152 that extends for all or substantially all of the length of drive ribbon 40B and a plurality of pegs 154 located within recess 152. Proximal edge section 58B defines a proximal edge surface 164 having a first axially facing lengthwise portion 166 and a second axially facing lengthwise portion 168. Distal edge section 56B includes a plurality of holes 156 and defines a distal edge surface 170 having a third axially facing lengthwise portion 172 and a fourth axially facing lengthwise portion 174. First and second axially facing surface portions 166, 168 face in an axial direction that is opposite than the axial direction faced by third and fourth axially facing surface portions 172, 174.

Figure 24:
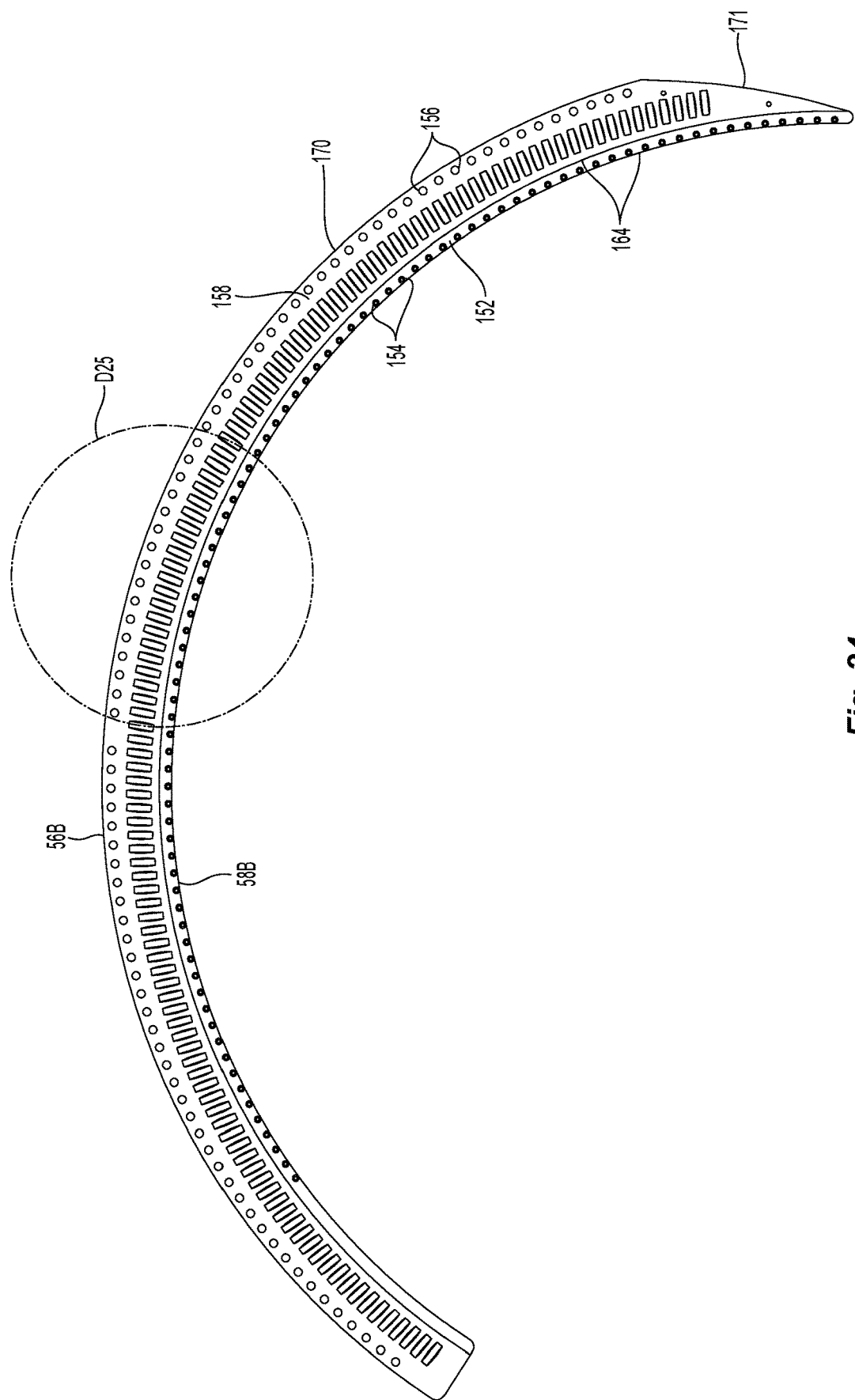
FIG. 24 is a top view of the drive ribbon of the embodiment of FIG. 21.
Figure 25A:
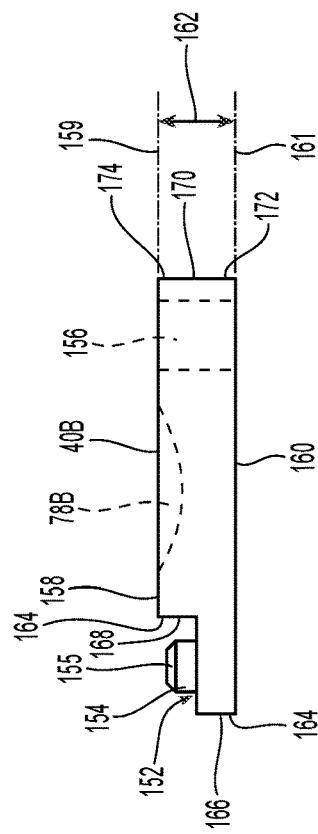
FIG. 25A is an end view of the drive ribbon of FIG. 24.
Figure 25:
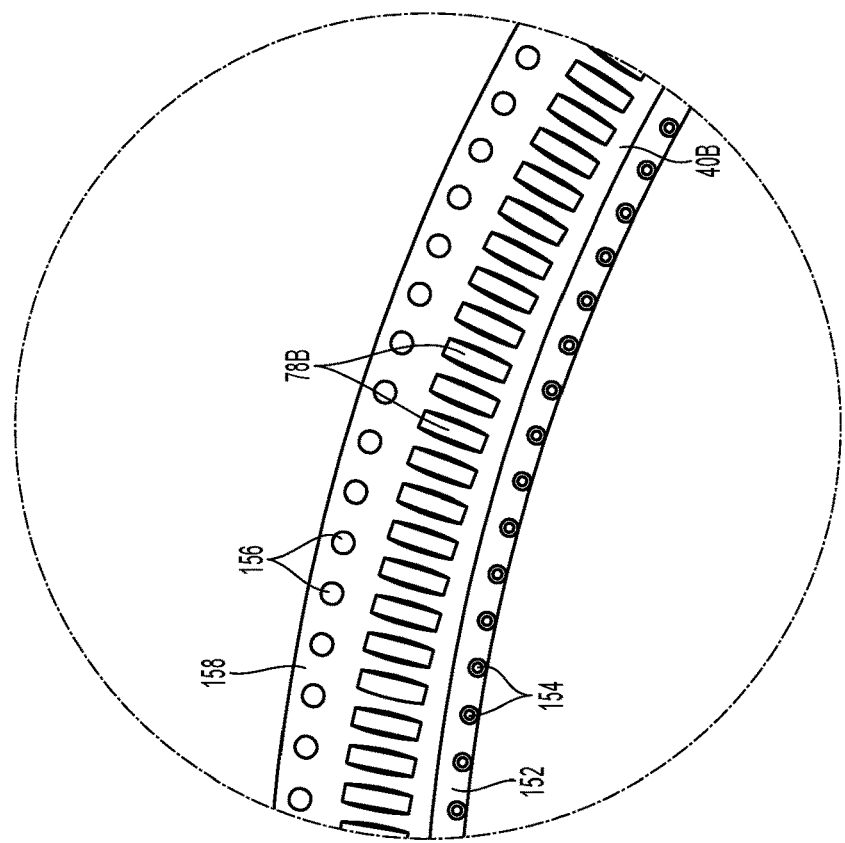
FIG. 25 is a view of detail D25 in FIG. 24.

FIG. 24 shows ribbon 40B in an unrolled condition and detail D25 is shown in FIG. 25. Another view of ribbon 40B is shown in FIG. 25A. As can be understood with reference to FIGS. 24, 25 and 25A, proximal edge surface 164 and distal edge surface 170 extend between first and second major surfaces 158, 160 and, when ribbon 40B forms a helix, are axially facing in opposite directions. First surface portion 166 extends lengthwise relative to ribbon 40B and is proximate second major surface 160 while second surface portion 168 extends lengthwise relative to ribbon 40B and is proximate first major surface 158.

In the illustrated embodiment, first portion 166 and second portion 168 are axially separated by recess 152. Third surface portion 172 extends lengthwise relative to ribbon 40B and is proximate second major surface 160 while fourth surface portion 174 extends lengthwise relative to ribbon 40B and is proximate first major surface 158. In the illustrated embodiment, third and fourth surface portions 172, 174 are coplanar. It is further noted that in the illustrated ribbon 40B, both the first and second major surfaces 158, 160 are parallel with the plane defined by drive ribbon 40B and the axially facing portions 166, 168, 172 and 174 of the proximal and distal edge surfaces 164, 170 are oriented perpendicular to the first and second major surfaces 172, 174.

Figure 26:
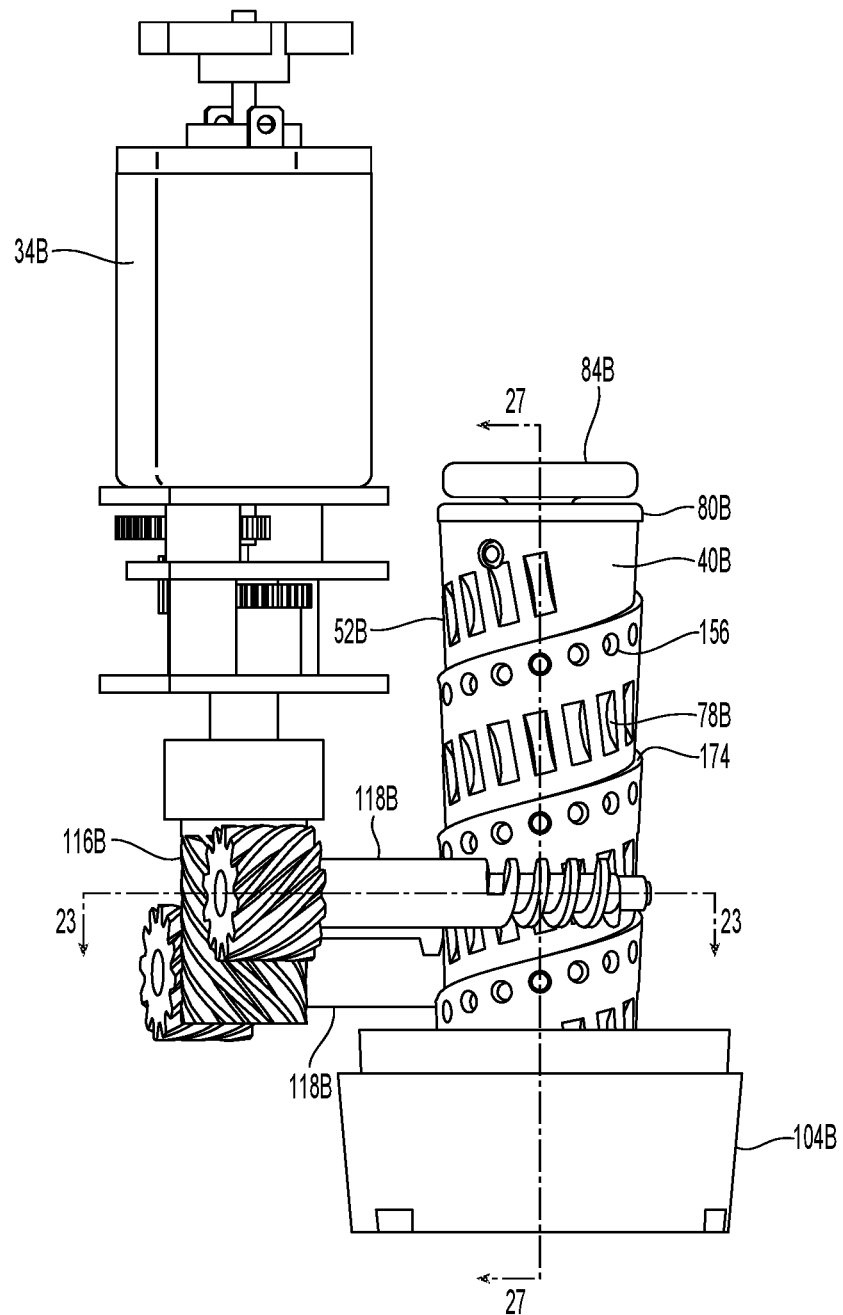
FIG. 26 is a side view of a portion of the embodiment of FIG. 21 with the housing removed.
Figure 27:
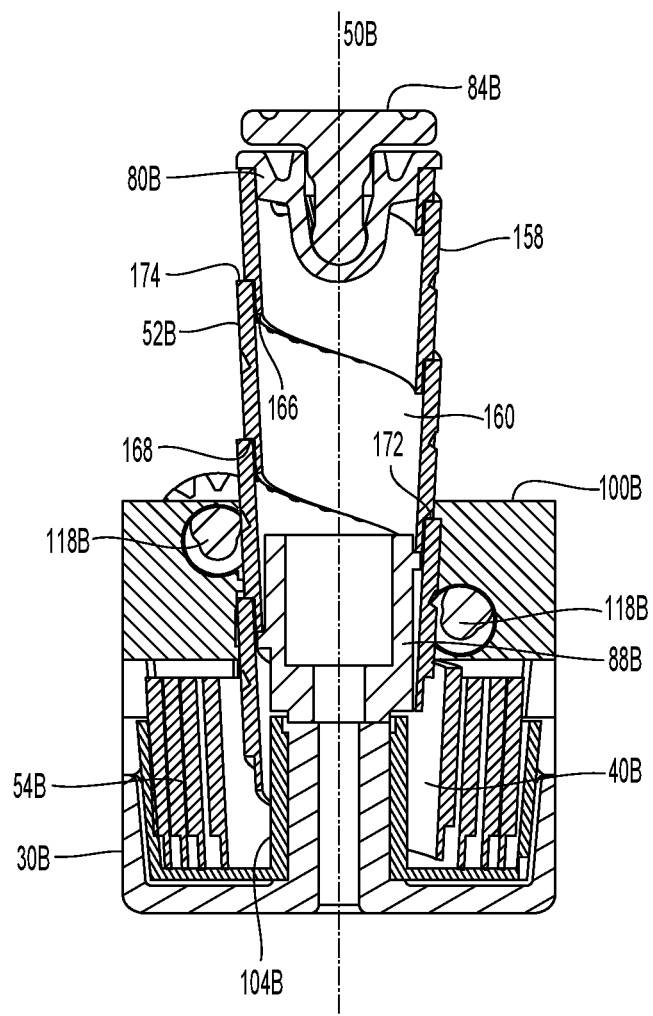
FIG. 27 is a cross sectional view taken along line 27-27 of FIG. 26 and also showing the ribbon bearing member.
Figure 28:
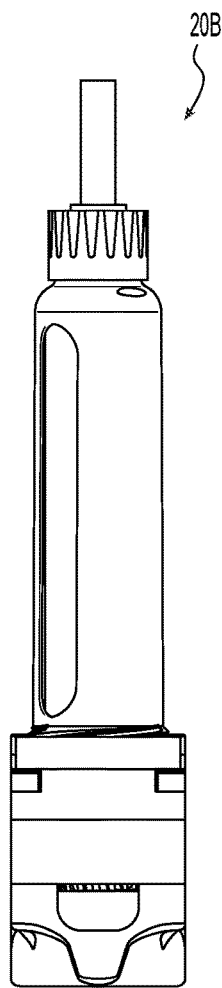
FIG. 28 is a side view of the embodiment of FIG. 21 with the housing removed.
Figure 30:
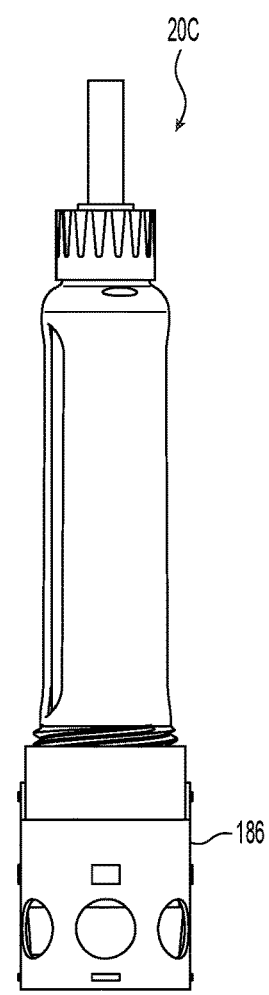
FIG. 30 is a side view of another embodiment with the housing removed.
Figure 29:
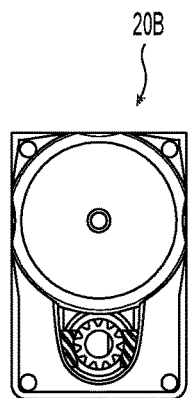
FIG. 29 is an end view of the embodiment of FIG. 21 with the housing removed.
Figure 31:
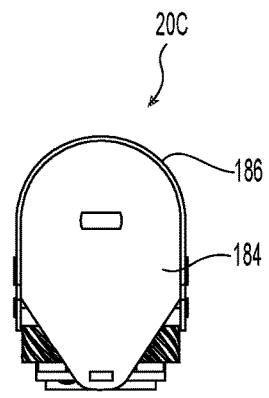
FIG. 31 is an end view of the embodiment of FIG. 30 with the housing removed.
Figure 32:
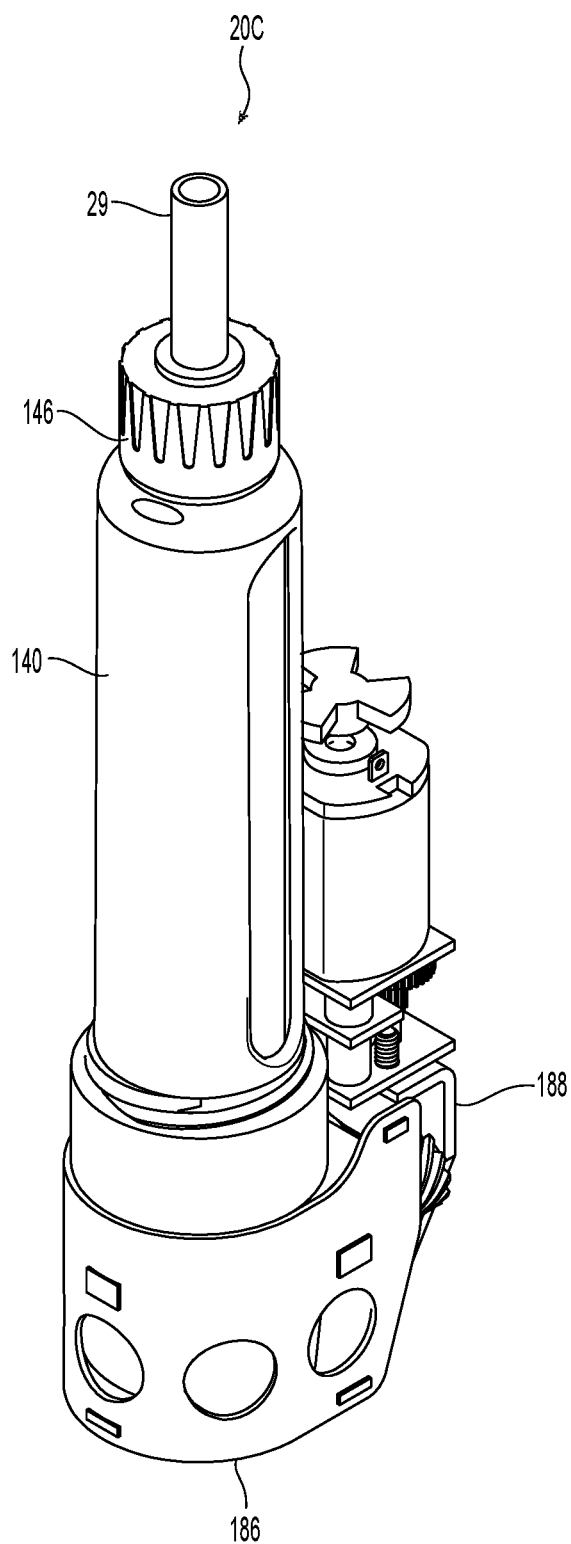
FIG. 32 is a perspective view of the embodiment of FIG. 30 with the housing removed.

As best understood with reference to FIGS. 26 and 27, in the extended portion of drive ribbon 40B that forms a helix, proximal edge section 58B is engaged with an adjacent portion of distal edge section 56B with the second axially facing lengthwise portion 168 of proximal edge surface 164 being engaged with the third axially facing lengthwise portion 172 of distal edge surface 170. The first axially facing lengthwise portion 166 of proximal edge surface 164 and the fourth axially facing lengthwise portion 174 of distal edge surface 170 extend radially outwardly in opposite directions. In the illustrated embodiment, the first axially facing lengthwise portion 166 extends radially inwardly while the fourth axially facing lengthwise portion 174 projects radially outwardly.

Thrust member 88B includes a helical thread 176 which is engaged with first axially facing lengthwise portion 166 of proximal edge surface 164. Helical thread 176 can engage surface 166 of drive ribbon 40B in the transition portion of drive ribbon 40B disposed between the retracted portion 54B defining a spiral and the extended portion 52B defining a helix of drive ribbon 40B. Because surface 166 projects radially and is still exposed in the extended portion 52B of drive ribbon 40B, helical thread 176 may also engage surface 166 in the helical extended portion 52B of drive ribbon 40B. Moreover, this arrangement also allows the helical thread 176 to engage surface 166 for more than 360 degrees about drive axis 50B. In the illustrated embodiment, helical thread 176 extends for greater than 360 degrees about axis 50B.

The ability of helical thread 176 to engage surface 166 after the engagement of the proximal edge section 58B with distal edge section 56B allows thread 176 to bear axial loads in the extended helical portion of the drive ribbon and thereby allow pegs 154 to mesh with holes 156 at a location where no axial load is being carried by drive ribbon 40B.

A ribbon bearing member 100B circumscribes the drive ribbon and defines a second helical thread 178 engageable with the fourth lengthwise portion 174 of distal edge surface 170. Thread 178 can engage surface portion 174 in the transition portion of drive ribbon 40B. However, because surface 174 projects radially and is still exposed in the extended portion 52B of drive ribbon 40B, helical thread 178 may also engage surface 174 in the helical extended portion 52B of drive ribbon 40B. This arrangement also allows helical thread 178 to engage surface 174 for more than 360 degrees about drive axis 50B. In the illustrated embodiment helical thread 178 extends for more than 360 degrees about drive axis 50B and circumscribes drive ribbon 40B proximate thrust member 88B. Ribbon bearing member 100B also supports gear members 118B and may be machined out of polyoxymethylene (POM), also known as acetal, polyacetal and polyformaldehydeor and sold under various tradenames such as Delrin, or formed using other suitable materials and methods.

By providing helical threads 176 and 178 which extend for more than 360 degrees about drive axis 50B and positioning the threads proximate each other, a short section of drive ribbon 40B is simultaneously constrained by both threads 176 and 178 thereby firmly controlling the axial position of the drive ribbon to facilitate the engagement of drive ribbon 40B with itself. The use of a helical thread 176 on thrust member 88B that extends for more than 360 degrees about drive axis 50B also increases the surface area over which compressive axial forces can be transferred between drive ribbon 40B and thrust member 88B.

Both thrust member 88B and ribbon bearing member 100B remain stationary relative to each other and support structure 30B while drive ribbon 40B rotates about drive axis 50B relative to these parts when drive ribbon 40B is being extended and retracted. Helical thread 176 on thrust member 88B bears against ribbon 40B to thereby bear axial compressive forces acting on the extended portion of drive ribbon 40B such as those generated when drive ribbon 40B axially pushes a piston 26 in a container 22. Helical thread 178 is engageable with portion 174 of distal edge surface 170 and thereby resists tensile forces acting on the drive ribbon 40B which would act to axially pull drive ribbon 40B away from thrust member 88B. Helical threads 176, 178 also axially align the drive ribbon with itself as the proximal edge section is engaged with an adjacent portion of the distal edge section as drive ribbon 40B is extended.

With regard to axially compressive forces, it is noted that the illustrated drive ribbon 40B is a unitary one-piece ribbon and all axial forces transferred between bearing member 80B and thrust member 88B when the drive ribbon is at least partially extended are transferred by the unitary one-piece drive ribbon 40B. Bearing member 80B includes two securement pegs 180 that are disposed in openings 182 in ribbon 40B. A transfer member 84B is rotatably mounted on bearing member 80B and engages piston 26 when using device 20B.

Bearing member 80B transfers axial forces to drive ribbon 40B through the engagement of pegs 180 with openings 182 and through an overlapping lip that engages distal end surface 171 of the distal end of drive ribbon 40B. The engagement of pegs 180 with openings 182 prevents the rotation of bearing member 80B relative to drive ribbon 40B. As drive ribbon 40B is extended, bearing member 80B will exert an axial force on piston 26 to thereby cause the discharge of medicament from container 22. In this regard, it is noted that bearing member 80B exerts this axial force on piston 26 through transfer member 84B which can rotate relative to bearing member 80B. Thus, during discharge of a medicament, transfer member 84B will bear on piston 26 and will not rotate relative to piston 26 but will rotate relative to bearing member 80B.

Axial compressive forces are transferred through ribbon 40B from bearing member 80B to thrust member 88B through the engagement of the second lengthwise portion of the proximal edge surface 168 with the third lengthwise portion of distal edge surface 172. Although the engagement of pegs 154 with holes 156 does not transfer compressive forces in the illustrated embodiment, alternative embodiments could utilize pegs and holes for this purpose. The engagement of the pegs 154 with holes 156 in the illustrated embodiment does, however, resist axially directed tensile forces acting on ribbon 40B and thereby resists the separation of extended ribbon.

A bobbin 104B is rotatable relative to thrust member 88B and the retracted portion 54B of drive ribbon 40B is stored in bobbin 40B. Bobbin 40B rotates along with drive ribbon 40B due to frictional engagement of drive ribbon 40B with bobbin 104B. In the illustrated embodiment, ribbon 40B is not attached to bobbin 104B. By not attaching ribbon 40B to bobbin 104B, the short length of ribbon that would be necessary to extend to and be secured with the bobbin when the drive ribbon is fully extended can be omitted. Various methods can be used to prevent the unsecured end of drive ribbon 40B from being overextended and having drive ribbon 40B escape from the drive mechanism. For example, the gear slots 78B can be terminated on the drive ribbon 40B at a location that will limit the extension of ribbon 40B. A stop in the form of a hook or other catch type member could alternatively or additionally be secured at the end of the drive ribbon that would prevent it from being moved through the gap between thrust member 88B and ribbon bearing member 100B. Alternatively, a controller which governs operation of the motor in a manner that limits the extension of drive ribbon 40B and prevents escape of the ribbon can be employed.

The use of a rotating bobbin 104B helps prevent friction lock of the retracted portion of the drive ribbon during extension and retraction of the drive ribbon. Alternative methods of preventing such friction lock, such as the use of a lubricous material to form the drive ribbon may alternatively be used and the rotating bobbin omitted.

In the illustrated version of drive ribbon 40B, a portion of the proximal edge surface projects radially inward while a portion of the distal edge surface projects radially outward. It is noted that other arrangements may also be used. For example, a portion of the proximal edge surface could project radially outward and a portion of the distal edge surface could project radially inward. In such an alternative embodiment, the helical thread engaging the proximal edge surface and bearing axially compressive forces would be positioned radially outward of the drive ribbon and the thread member engaging a portion of the distal edge surface and positioned to resist axial tensile forces would be positioned radially inward of the drive ribbon.

The offset arrangement of the edge surfaces causes one of the edge surfaces to have a longer length per unit length of drive ribbon. In the illustrated embodiment, it is the distal edge that has a relatively longer length. When drive ribbon 40B is unrolled and positioned in a plane as depicted in FIG. 24, drive ribbon 40B defines an arc with proximal edge section 58B positioned radially inward of distal edge section 56B. In embodiments where the proximal edge projects radially outward, the proximal edge section will be positioned radially outward of the distal edge section when the ribbon is positioned in a plane to define an arc.

Another embodiment 20C similar to device 20B but having a slightly slimmer profile is shown in FIGS. 30-33. Device 20C differs from device 20B by employing several sheet metal parts that allow for a reduction in the size of housing support structure. More specifically, a metal base plate 184, a metal skirt 186 and a metal support bracket 188 are utilized in device 20C.

As most easily seen in FIG. 33, the motor, gearing, drive ribbon and bobbin are the same as those used in device 20B. Ribbon bearing member 100C has a slightly different shape but functions in the same manner as ribbon bearing member 100B. As can be seen in FIG. 33, ribbon bearing member 100C includes threads 190 for engaging threads 148 of cartridge sleeve 140. Although not shown in the figures for purposes of graphical clarity, ribbon bearing member 100B includes similar threads for engaging cartridge sleeve 140. Thrust member 88C includes a post 192. A key 194 on post 192 engages a keyway 196 on baseplate 184 and prevents relative rotation of post 192 and the support structure of which baseplate 184 is a part. Bobbin 104C is rotatably disposed on post 192 and a washer 198 encircling post 192 is located between baseplate 184 and bobbin 104C to separate bobbin 104C from baseplate 184.

Devices 20 and 20A-20C can be provided with or without what is generally referred to as force feedback. Force feedback determines the force acting on piston 26 and thereby allows the device to know the state of container 22 and/or position of piston 26.

If the user is relied upon for priming and otherwise confirming the state of the device, force feedback is not needed. In a device without force feedback, motor speed and current can be monitored to determine the state of the system and avoid applying excessive torque to ribbon 40 and hence excessive force to piston 26. It may be possible that the current-sensing signal-to-noise ratio will be sufficient to detect contact between distal end of the drive ribbon and piston 26. Generally, the system will initiate and complete each dose with the system open to atmospheric pressure through outlet 28. In such a system, sensing the force on piston 26, i.e., force feedback, is not necessary for dosing accuracy.

If a force feedback system is used, the device will know when the distal end of transfer member 84 contacts piston 26. This will allow some user steps, such as priming, to be fully or partially automated. A simple force feedback system could employ a contact switch that triggers at a low force. Such a switch could be located at the distal end 81 of the drive ribbon and coupled with bearing member 80 or rotational bearing 82. Electrical conductors could be disposed on the drive ribbon to provide electrical communication between the contact switch and a processor within the housing. Proportional force sensing is also possible by using a force-sensing component such as a force sensitive resistor instead of a contact switch. The conductors disposed on the drive ribbon could terminate in or on the storage bobbin. If a rotating bobbin is used, a continuous connection to the device frame can be provided by slip rings or other appropriate contacts.

The illustrated embodiments are electro-mechanical and controlled by a processor, microcontroller or microcomputer. The use of a processor allows numerous interaction points and additional functions to be incorporated in the device. For example, the user can interact with the device using a touchscreen, a multiple-button interface, or specific touch points (such as a dose-setting wheel). If desired, such controls could mimic the interaction behaviors of conventional injection devices.

The device could also display a variety of different information such as current dose setting, last dose, reminders and use cues or any other useful information. The displays may take the form of a liquid crystal display (LCD), organic light-emitting diode (OLED), electronic paper display (EPD), or other suitable display.

The device can also be provided with connectivity allowing it to connect to and interact with other devices (e.g. smart phones) using either wired or wireless communication techniques. These interactions can be used to exchange information in either direction, allowing (for instance) a health care practitioner to change device settings or download dosing history.

While this invention has been described as having an exemplary design, the present invention may be further modified within the spirit and scope of this disclosure. This application is therefore intended to cover any variations, uses, or adaptations of the invention using its general principles.

What is claimed is:

1. A ribbon used within a container to advance a piston along a drive axis within the container, the ribbon, comprising:
a body having a proximal edge and a distal edge, the body capable of forming a coiled shape about the drive axis, and having an interior surface facing the drive axis and an exterior surface facing away from the drive axis,
one of the proximal edge and the distal edge having a plurality of first engageable features, and
the other of the proximal edge and the distal edge having a plurality of second engageable features,
wherein, in response to a section of the body in the coiled shape forming an interlocked configuration, a portion of the proximal edge of said section is engaged with an adjacent portion of the distal edge of said section, and each of the plurality of first engageable features is configured to couple to a corresponding one of the plurality of second engageable features along said section.

2. The ribbon of claim 1, wherein the body in the coiled shape defines a distal end, the ribbon further comprising a bearing member supported by the distal end.

3. The ribbon of claim 2 further comprising a transfer member rotatably mounted to the bearing member.

4. The ribbon of claim 1, wherein a plurality of teeth is formed along the interior surface, the plurality of teeth configured to engage a mechanical drive that is configured to transmit a rotational force through the plurality of teeth to the body.

5. The ribbon of claim 1, wherein a plurality of teeth is formed along the exterior surface, the plurality of teeth configured to engage a mechanical drive that is configured to transmit a rotational force through the plurality of teeth to the body.

6. The ribbon of claim 1, wherein the plurality of first engageable features comprises recesses, and the plurality of second engageable comprises projections, the proximal edge has the plurality of recesses, and the distal edge has the plurality of projections.

7. The ribbon of claim 1 wherein the plurality of first engageable features comprises projections, and the plurality of second engageable comprises recesses, the distal edge has the plurality of recesses, and the proximal edge has the plurality of projections.

8. The ribbon of claim 1, wherein one of the proximal edge and the distal edge defines a radially extending lip.

9. The ribbon of claim 1, wherein one of the proximal edge and the distal edge defines a radially inward extending flange, and the other of the proximal edge and the distal edge defines a radially outward extending flange that is engageable with the radially inward extending flange when said section of the body forms the interlocked configuration.

10. The ribbon of claim 1, wherein one of the plurality of first engageable features and the plurality of second engageable features comprises projections that extend radially.

11. A drive assembly for a medication delivery device, comprising:
a ribbon comprising a body having a proximal edge and a distal edge, the body capable of forming a coiled shape about the drive axis, and having an interior surface facing the drive axis and an exterior surface facing away from the drive axis, one of the proximal edge and the distal edge having a plurality of first engageable features, and the other of the proximal edge and the distal edge having a plurality of second engageable features, wherein, in response to a section of the body in the coiled shape forming an interlocked configuration, a portion of the proximal edge of said section is engaged with an adjacent portion of the distal edge of said section, and each of the plurality of first engageable features is configured to couple to a corresponding one of the plurality of second engageable features along said section; and a mechanical drive having a gearing arrangement engaged with a plurality of teeth of the drive ribbon, and a motor operative to rotate the mechanical drive, wherein, in response to rotation of the mechanical drive, the section of the ribbon in the interlocked configuration extends farther to advance the piston within the container.

12. The drive assembly of claim 11, wherein the plurality of teeth is formed along the interior surface, and a drive gear of the gearing arrangement is internal to the body of the ribbon in the coiled shape and configured to engage the plurality of teeth and transmit a rotational force to the body.

13. The drive assembly of claim 11, wherein one of the plurality of first and second engageable features comprises recesses, and the other of the plurality of first and second engageable features comprises projections.

14. The drive assembly of claim 11, wherein the plurality of teeth is formed along the exterior surface, and a drive gear of the gearing arrangement is external to the body of the ribbon in the coiled shape and configured to engage the plurality of teeth and transmit a rotational force to the body.

15. A medication delivery device, comprising:
a container to hold a medicament and defining an outlet, the container further including a piston disposed within the container;
a ribbon comprising a body having a proximal edge and a distal edge, the body capable of forming a coiled shape about the drive axis, and having an interior surface facing the drive axis and an exterior surface facing away from the drive axis, one of the proximal edge and the distal edge having a plurality of first engageable features, and the other of the proximal edge and the distal edge having a plurality of second engageable features, wherein, in response to a section of the body in the coiled shape forming an interlocked configuration, a portion of the proximal edge of said section is engaged with an adjacent portion of the distal edge of said section, and each of the plurality of first engageable features is configured to couple to a corresponding one of the plurality of second engageable features along said section; and a mechanical drive having a gearing arrangement engaged with a plurality of teeth of the drive ribbon, and a motor operative to rotate the mechanical drive, wherein, in response to rotation of the mechanical drive, the section of the ribbon in the interlocked configuration extends farther to advance the piston within the container to expel medicament through the outlet.

16. The device of claim 15, wherein the mechanical drive includes a worm gear.

17. The device of claim 15, wherein the mechanical drive includes a gear member.

18. The device of claim 15, wherein the gear member is disposed internal to the body in the coiled shape.

19. The device of claim 15, wherein a gear of the gearing arrangement is configured to engage the plurality of teeth and transmit a rotational force to the body.

20. The device of claim 15, wherein the container holds the medicament.

* * * * *